US010532346B2

(12) United States Patent
Durante et al.

(10) Patent No.: US 10,532,346 B2
(45) Date of Patent: *Jan. 14, 2020

(54) METHOD FOR PRODUCING A METAL-SUPPORTED CATALYST AND CATALYST SUBSTRATE

(71) Applicant: ALLOY SURFACES COMPANY, INC., Chester Township, PA (US)

(72) Inventors: Vincent A. Durante, West Chester, PA (US); Rajinder Gill, West Grove, PA (US); Andrew Davis, Swarthmore, PA (US); Elaine C. Soltani, West Chester, PA (US)

(73) Assignee: ALLOY SURFACES COMPANY, INC., Chester Township, PA (US)

( * ) Notice: Subject to any disclaimer, the term of this patent is extended or adjusted under 35 U.S.C. 154(b) by 685 days.

This patent is subject to a terminal disclaimer.

(21) Appl. No.: 15/239,210

(22) Filed: Aug. 17, 2016

(65) Prior Publication Data

US 2016/0354767 A1    Dec. 8, 2016

Related U.S. Application Data

(62) Division of application No. 13/649,622, filed on Oct. 11, 2012, now Pat. No. 9,446,386.

(51) Int. Cl.
*B01J 21/02* (2006.01)
*B01J 23/44* (2006.01)
(Continued)

(52) U.S. Cl.
CPC ............. *B01J 23/894* (2013.01); *B01J 21/02* (2013.01); *B01J 23/44* (2013.01); *B01J 23/63* (2013.01);
(Continued)

(58) Field of Classification Search
CPC .......... B01L 21/02; B01L 23/44; B01L 23/63; B01L 23/755; B01L 23/80;
(Continued)

(56) References Cited

U.S. PATENT DOCUMENTS 4,443,557 A * 4/1984 Baldi ...................... B01J 23/892
502/301
4,927,798 A * 5/1990 Baldi ...................... B65D 43/022
502/301

(Continued)

OTHER PUBLICATIONS

Notification of Transmittal of the International Search Report and the Written Opinion of the International Searching Authority, or the Declaration; International Search Report; Written Opinion of the International Searching Authority, International Application No. PCT/US2013/063857.

*Primary Examiner* — Cam N. Nguyen
(74) *Attorney, Agent, or Firm* — Polsinelli PC

(57) ABSTRACT

The present invention relates to methods for producing metal-supported thin layer skeletal catalyst structures, to methods for producing catalyst support structures without separately applying an intermediate washcoat layer, and to novel catalyst compositions produced by these methods. Catalyst precursors may be interdiffused with the underlying metal support then activated to create catalytically active skeletal alloy surfaces. The resulting metal-anchored skeletal layers provide increased conversion per geometric area compared to conversions from other types of supported alloy catalysts of similar bulk compositions, and provide resistance to activity loss when used under severe on-stream conditions. Particular compositions of the metal-supported skeletal catalyst alloy structures can be used for conventional steam methane reforming to produce syngas from natural gas and steam, for hydrodeoxygenation of pyrolysis bio-oils, and for other metal-catalyzed reactions inter alia.

17 Claims, 9 Drawing Sheets

(51) Int. Cl.
   *B01J 23/63*   (2006.01)
   *B01J 23/755*  (2006.01)
   *B01J 23/80*   (2006.01)
   *B01J 23/84*   (2006.01)
   *B01J 23/86*   (2006.01)
   *B01J 23/89*   (2006.01)
   *B01J 25/00*   (2006.01)
   *B01J 25/02*   (2006.01)
   *B01J 32/00*   (2006.01)
   *B01J 35/00*   (2006.01)
   *B01J 35/06*   (2006.01)
   *B01J 35/10*   (2006.01)
   *B01J 37/02*   (2006.01)
   *B01J 37/06*   (2006.01)
   *B01J 37/08*   (2006.01)
   *B01J 37/14*   (2006.01)
   *B01J 37/18*   (2006.01)
   *C01B 3/40*    (2006.01)
   *C07C 5/03*    (2006.01)
   *B01J 23/847*  (2006.01)
   *C10G 2/00*    (2006.01)
   *C10G 3/00*    (2006.01)

(52) U.S. Cl.
   CPC ............. *B01J 23/755* (2013.01); *B01J 23/80* (2013.01); *B01J 23/8472* (2013.01); *B01J 23/8476* (2013.01); *B01J 23/866* (2013.01); *B01J 23/8906* (2013.01); *B01J 25/02* (2013.01); *B01J 32/00* (2013.01); *B01J 35/06* (2013.01); *B01J 35/1019* (2013.01); *B01J 37/0225* (2013.01); *B01J 37/0228* (2013.01); *B01J 37/06* (2013.01); *B01J 37/14* (2013.01); *B01J 37/18* (2013.01); *C01B 3/40* (2013.01); *C07C 5/03* (2013.01); *C10G 2/332* (2013.01); *C10G 2/333* (2013.01); *C10G 3/45* (2013.01); *C10G 3/47* (2013.01); *C01B 2203/0233* (2013.01); *C01B 2203/107* (2013.01); *C01B 2203/1041* (2013.01); *C01B 2203/1058* (2013.01); *C01B 2203/1064* (2013.01); *C01B 2203/1076* (2013.01); *C01B 2203/1082* (2013.01); *C01B 2203/1235* (2013.01); *C01B 2203/1241* (2013.01); *C07C 2521/02* (2013.01); *C07C 2521/06* (2013.01); *C07C 2523/44* (2013.01); *C07C 2523/63* (2013.01); *C07C 2523/755* (2013.01); *C07C 2523/89* (2013.01)

(58) Field of Classification Search
   CPC ............. B01L 23/8472; B01L 23/8476; B01L 23/866; B01L 23/894; B01L 23/8906; B01L 25/00; B01L 25/02; B01L 35/002; B01L 35/06; B01L 35/1019; B01L 37/0217; B01L 37/0225; B01L 37/0228; B01L 37/06; B01L 37/08; B01L 37/14; B01L 37/18; B01J 32/00; C01B 3/40; C07C 5/03; C10G 2/331; C10G 2/332; C10G 2/333; C10G 3/44; C10G 3/45; C10G 3/47; C10G 3/48; C10G 45/36; C10G 45/38; C10G 49/04
   See application file for complete search history.

(56) References Cited

U.S. PATENT DOCUMENTS

| | | | |
|---|---|---|---|
| 5,464,699 A * | 11/1995 | Baldi | B01J 25/00 102/364 |
| 6,406,561 B1 | 6/2002 | Creech et al. | |
| 8,277,773 B2 * | 10/2012 | Watson | B01J 23/464 423/594.16 |
| 2005/0239643 A1 | 10/2005 | Benderly et al. | |
| 2008/0308457 A1 | 12/2008 | Dindi et al. | |

* cited by examiner

| PROCESS EMBODIMENT 1 | PROCESS EMBODIMENT 2 |
|---|---|
| SLURRY PREPARATION AND BALL MILLING<br>↓<br>SIX INCH WIDE COATING OF SLURRY ON SIX INCH WIDE Ni STOCK FOIL (CLEANED)<br>↓<br>FURNACING<br>↓<br>RECOIL<br>↓<br>CONTINUOUS LEACH<br>↓<br>CHELATING ACID BATH<br>↓<br>CONTINUOUS ABRASION<br>↓<br>CONTINUOUS PASSIVATION<br>↓<br>CONTINUOUS RINSE/WASH<br>↓<br>CONTINUOUS DRY<br>↓<br>SLITTING, CHOPPING AND CORRUGATION<br>↓<br>COMBINING PIECES TO PREPARE SHAPED BODY<br>↓<br>PACKAGING | SLURRY PREPARATION AND BALL MILLING<br>↓<br>SIX INCH WIDE COATING OF SLURRY ON SIX INCH WIDE Ni STOCK FOIL (CLEANED)<br>↓<br>FURNACING<br>↓<br>SLITTING, CHOPPING AND CORRUGATION<br>↓<br>COMBINING PIECES TO PREPARE SHAPED BODY<br>↓<br>LEACH AS A FORMED SHAPE<br>↓<br>CHELATING ACID BATH<br>↓<br>ABRASION AS A FORMED SHAPE<br>↓<br>PASSIVATE<br>↓<br>RINSE/WASH<br>↓<br>DRY<br>↓<br>PACKAGING |

Figure 1

ASC-54-18-1  ASC-54-18-2

METHOD FOR PRODUCING A METAL-SUPPORTED CATALYST AND CATALYST SUBSTRATE

FIELD OF THE INVENTION

The present invention relates to methods for producing metal-supported thin layer skeletal catalyst structures, to methods for producing catalyst support structures without separately applying an intermediate washcoat layer, and to novel catalyst compositions produced by these methods. Catalyst precursors may be interdiffused with the underlying metal support then activated to create catalytically active skeletal alloy surfaces. The resulting metal-anchored skeletal layers provide increased conversion per geometric area compared to conversions from other types of supported alloy catalysts of similar bulk compositions, and provide resistance to activity loss when used under severe on-stream conditions. Particular compositions of the metal-supported skeletal catalyst alloy structures can be used for conventional steam methane reforming to produce syngas from natural gas and steam, for hydrodeoxygenation of pyrolysis bio-oils, and for other metal-catalyzed reactions inter alia. The interdiffused alloy surfaces optionally may be formed into bulk monolithic structures (before or after activation) and further treated in an oxidation step to generate adherent oxide layers that provide intrinsic support surfaces for secondarily applied catalytic agents such as dispersed precious or platinum group metals. Metal substrate form factors such as fibers can be treated by the methods described herein to generate adherent thin-layer skeletal catalysts and/or catalyst supports, which, in turn, can be fabricated into structures of high geometric-surface-area-to-volume ratios.

BACKGROUND

Intensified processing methodologies are used increasingly in place of traditional chemical processing routes when small production volumes are warranted or when portability of process equipment is desired. For example, large scale hydroprocessing of biofuels derived from local sources is impractical for isolated military units in remote locations. Instead, portable conversion units and/or units with small footprints are needed. However large scale processing reactors are not easily downscaled for such uses. Thus, the need exists for competent catalysts and corresponding reactor configurations that are suitable for on-site process chemistry in small, modular units.

Simply operating established heterogeneous catalysts in compact reactor configurations at higher space velocities and at more severe temperatures than used in traditional processing will not necessarily increase productivity as needed. Under such modified conditions, mass and heat transfer limitations attenuate maximum catalyst activity, especially when such processes are conducted in traditional reactor designs. Consequently, intrinsically fast catalytic cycles alone afford no additional productivity benefits without addressing the mass and heat transfer limitations.

A variety of different shapes and styles of heterogeneous catalysts are currently available that seek to augment the ratio of geometric surface area to occupied reactor volume as a means of mitigating mass and heat transfer limitations. Preformed metallic scaffolding structures are preferred over ceramic scaffolding structures when very thin walls or low pressure drop is needed in densely packed channel structures such as those desirable for intensified processing. In particular, microchannel constructs, such as thin-walled metallic honeycombs, covered with a minimally thick catalytic layer, have been sought to decrease resistance between process fluids and channel walls thereby promoting rapid convective heat and mass transfer as well as conductive heat transfer.

The ratio of surface atoms exposed to process fluids to total atoms of a catalytically active metal cluster is termed "dispersion" for the purposes of this discussion. Catalyst support surfaces that enable high dispersion of applied catalytic agents are sought in the art. To reduce required content of costly catalytic components and to achieve sufficiently high dispersion to promote high catalytic activity per structural unit, base metal or precious or platinum group metal heterogeneous catalysts usually are applied to catalyst support materials, often composed of high surface area oxide powders. Typically, structured catalyst supports are produced by applying an intermediate washcoat layer of inert metal oxide or aqueous hydroxide slurries directly onto metal foils that have been preformed into a desired scaffolding structure. A second application of precursors transformable to reduced metal clusters, e.g. alcoholic or aqueous solutions of metal salts, is usually applied afterward. Alternatively, the metal salts can be admixed with the oxide or hydroxide aqueous slurries and applied in one step to the metal substrate. Catalytically active metals or active compounds are thereby distributed within the washcoat layer, rather than in exclusive direct contact with bare metal substrate. The active material therefore sits on the surface of the intermediate washcoat layer and is insulated from the underlying metallic substrate. As such, the washcoating is susceptible to damage, such as delamination, from aggressive physical manipulation and/or intensified process conditions because the coating is only weakly adhered to the underlying metal scaffolding structure. These catalyst structures usually are coated after physical forming of the scaffold to minimize damage to the cured catalyst coatings that could result if mechanical processing were done after application of the washcoat.

The application of slurries to preformed substrates also can result in the coating having a nonuniform distribution. Preformed substrates are normally dip-coated or spray-coated with the washcoat slurry, and excess slurry is removed using an air knife. Excess slurry is difficult to remove from small crevices and corners, particularly in catalyst structures containing microchannels, and can result in varying thicknesses of the washcoat throughout the catalyst structure, which leads to a catalyst layer of varying thickness on the substrate.

When such a supported catalyst is used to accelerate an exothermic reaction, e.g. catalytic oxidation of entrapped soot particles or of gaseous hydrocarbons, the varying thickness of the catalyst could result in hot spots forming in the catalyst layer, which in turn can cause melting of the substrate or sintering of the active phase, thereby prematurely reducing dispersion and corresponding activity. An alternative to the use of high surface area supported base metals as catalysts is the possibility for use of bulk skeletal metal aggregates, such as Raney metals, to prepare highly active catalysts. These skeletal metal particles typically are used in slurry phase processing or, less commonly, in packed beds. The latter usually suffer from pressure drop or particulation problems in practical use. Small channel monolith structures containing bound bulk skeletal metal catalysts, which in principle could generate a diminished pressure drop compared to packed beds under high space velocity conditions, would be difficult and costly to fabricate. Furthermore, under severe process conditions, such as encountered in steam methane reforming for example, bulk skeletal metal aggregates would rapidly deactivate due to surface sintering or easily delaminate from their underlying scaffolding, if used.

SUMMARY OF THE INVENTION

Accordingly, the present invention addresses problems and expands the applications in the prior art and, in a first manifestation, provides a method of producing an intrinsically bound thin-layer skeletal catalyst-coated metal foil or fiber with relatively uniform coating thickness capable of physical manipulation into a highly active catalytic monolithic structure, without requiring separate application of an intermediate washcoat or additional catalytic agents.

In particular, a first aspect of the present invention is a method for making a catalyst, comprising the following steps:

(a) preparing a slurry comprising one or more metal (including prealloyed) powders including aluminum;

(b) coating a flat metal substrate or a flattened mat of metal fiber or a flattened woven metal fiber assembly with said slurry;

(c) subjecting the coated metal substrate or coated metal fiber mat or coated woven metal fiber assembly to heat under an inert or reducing atmosphere whereby at least one of the one or more metal powders melts and interdiffuses into the surface of the flat metal substrate or metal fiber mat or woven metal fiber assembly;

(d) leaching the coated metal substrate or coated metal fiber mat or coated woven metal fiber assembly obtained in step (c) in a caustic solution;

(e) bathing the coated metal substrate, coated metal fiber mat or coated woven metal fiber assembly obtained in step (d) in a chelating acid solution;

(f) passivating the coated metal substrate, coated metal fiber mat or coated woven metal fiber assembly obtained in step (e); and (g) optionally abrading the surface of the coated metal substrate, coated metal fiber mat or coated woven metal fiber assembly obtained in step (f).

The coated metal substrate or coated metal fiber mat or coated woven metal fiber assembly obtained at the end of step (c) is physically manipulated into a desired form for the final catalyst either: after step (c) and before the leaching step; or after the passivating step.

In step (c) of the above-described process, the coated metal substrate, coated metal fiber mat or coated woven metal fiber assembly is heated to a temperature in the range of about 600-1100° C., preferably from about 650-910° C., for a period of time of from about 0.2 to 4 minutes, preferably from about 0.3 to 1 minute. The specific processing conditions are varied depending on the compositions of the metal substrate or metal fiber mat or woven metal fiber assembly used, its thickness, and on the alloy to be formed on the surface. The layered structure of the finished catalyst consists essentially of an upper layer of skeletal metals or alloys that has been optionally partly abraded, an interdiffusion layer that has been optionally partly exposed, and a residual substrate core (i.e., where the metal substrate core is usually the original metal of the metal substrate or the original metal that made up the metal fibers in the metal fiber mat or woven metal fiber assembly).

If coiled stock is desired, steps (b) through (g) optionally can be integrated into a semi-continuous web process in which a continuously moving web of substrate material (i.e., here, the substrate material can be a flat metal foil or a flattened metal fiber mat or a flattened woven metal fiber assembly) passes from one unit operation step to the next, or with optional intermediate recoiling, until all steps are completed. If honeycomb or similar structured scaffolding form factors are desired, forming and/or fastening steps preferably can be introduced after step (c) or after step (g), with subsequent processing conducted on individual parts rather than in a web process.

A second aspect of the present invention is a method for making a catalyst support structure wherein an intrinsic oxidic support layer is deliberately produced. The method comprises the following steps:

(a) preparing a slurry comprising one or more metal (including prealloyed) powders including aluminum;

(b) coating a flat metal substrate or a flattened metal fiber mat or a flattened woven metal fiber assembly with said slurry;

(c) subjecting the coated metal substrate or coated metal fiber mat or coated woven metal fiber assembly to heat under a reducing atmosphere whereby at least one of the one or more metal powders melts and interdiffuses into the surface of the metal substrate or metal fiber mat or woven metal fiber assembly;

(d) optionally leaching the coated metal substrate or coated metal fiber mat or coated woven metal fiber assembly obtained in step (c) in a caustic solution;

(e) subjecting the coated and heat treated metal substrate, metal fiber mat or woven metal fiber assembly obtained in step (c) or (d), if practiced, to heat in an oxygen containing atmosphere for an additional period of time.

Subjecting the coated and heat treated metal substrate, metal fiber mat or woven metal fiber assembly to heat for a second period of time in an oxygen containing atmosphere (i.e., step (e) above) can produce an alumina or mixed metal oxide intrinsic catalyst support layer that is more strongly adhered to the coated metal substrate, coated metal fiber mat or coated woven metal fiber assembly and has a more uniform thickness distribution than a washcoat layer that is obtained from a traditional spray or dip coating process using a slurry mainly composed of metal oxides, applied to fully formed monolithic structural units. Catalytic species, such as precious or platinum group metals, can be dispersed on or into the intrinsic oxidic support layer using known methods. The temperature used in step (e) is from about 400 to 950° C., preferably from about 640 to 850° C. The amount of time that the coated metal substrate, coated metal fiber mat or coated woven metal fiber assembly is held at those temperatures is from about 10 to 600 minutes, preferably from about 45 to 180 minutes.

In step (c) of the above-described process, the coated metal substrate, coated metal fiber mat or coated woven metal fiber assembly is heated to a temperature in the range of about 640-1100° C., preferably from about 650-900° C., for a period of time from about 0.2 to 4 minutes, preferably from about 0.3 to 1 minute.

We contemplate that steps (b) through (e) optionally can be integrated into a semi-continuous web process in which a continuously moving web of substrate material (i.e., metal foil or flattened metal fiber mat or flattened woven metal fiber assembly) passes from one unit operation step to the next, or with optional intermediate recoiling, until all steps are completed. If honeycomb or similar structured scaffolding form factors are desired, forming and/or fastening steps can be introduced most advantageously after step (c), with subsequent processing conducted on individual parts rather than in a web process.

Yet another aspect of the present invention involves particular macroporous multimetallic alloy or mixed metal formulations (i.e., on the surface of a metal substrate) made during the disclosed processes for making thin layer skeletal metal structured catalysts. The alloy or mixed metal formulations are particularly useful for conventional steam methane reformation to produce syngas from natural gas and steam, and for hydrodeoxygenation of pyrolysis bio-oils, and yet inherently resistant to sintering. Other uses for the catalysts of the present invention include: (a) Fischer-Tropsch synthesis reactions (particularly Fe—Co—Zr—Al catalysts); (b) hydrogenations of fatty acids (particularly over Ni—Zr—B—Al or Ni—Cr—B—Al catalysts); and (c) partial oxidations of aromatics (particularly Au—Ni—Zr—Al catalysts).

BRIEF DESCRIPTION OF THE DRAWINGS

FIG. 1 is a schematic of two embodiments of the present process to make a metal-supported catalyst structure.

DETAILED DESCRIPTION OF THE INVENTION

Figure 2A:
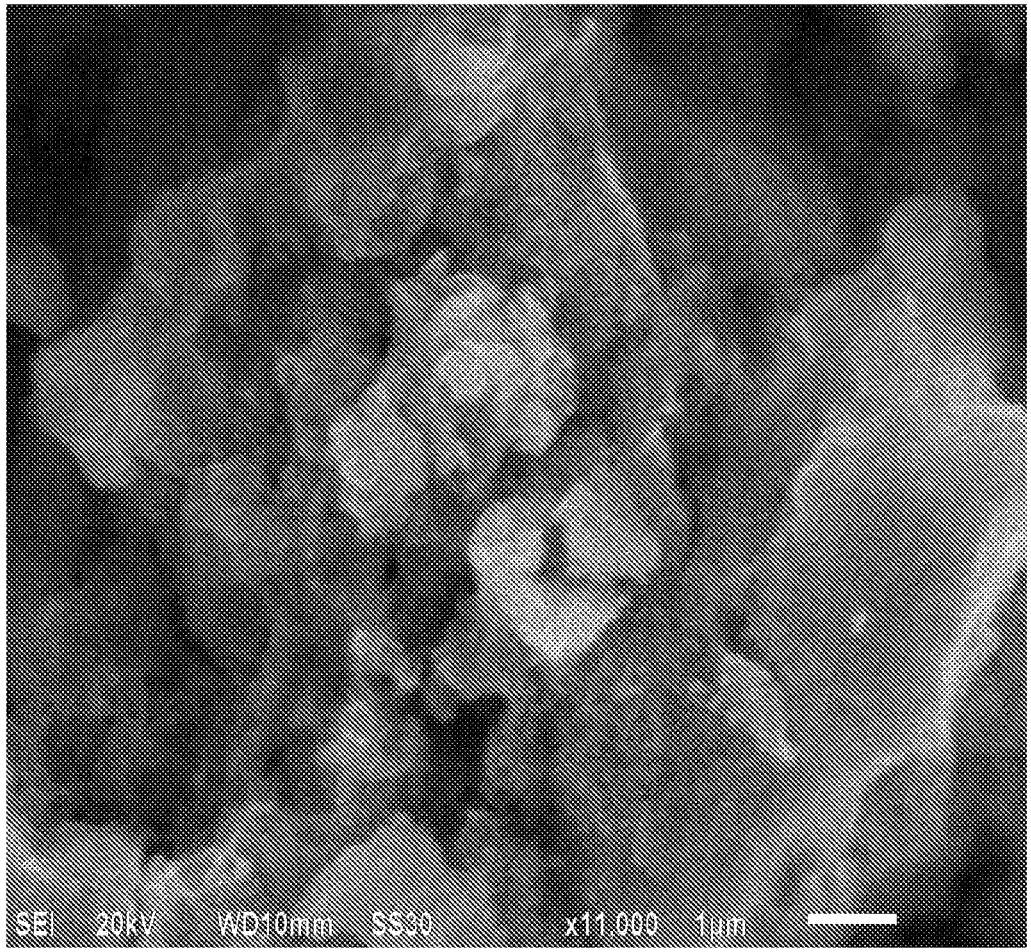
FIGS. 2A, 2B and 2C are scanning electron microscope images showing a comparison of the surfaces of fresh (passivated) catalyst (2A), steamed (i.e., at 900° C. for 9 hours) catalyst (2B), and used catalyst that had been on stream for several hundred hours (2C).

The present invention will be understood by those skilled in the art by reference to the following description of the preferred embodiments including examples and the accompanying drawings.

In a first embodiment, this invention relates to a method for producing thin-layer skeletal catalyst-coated metal and metal alloy structures without applying an intermediate washcoat layer and, in a second embodiment, to a method for generating an adherent oxidic layer on a thin metal foil or fibrous substrate, suitable as a catalyst support, without applying an additional oxide slurry washcoat. Other aspects of this invention relate to the formation and use of specific catalytically active skeletal metal layers whose compositions consist of particular surface alloys or multiple metal mixtures produced by the method of the first embodiment.

FIG. 1 is a schematic of two embodiments of the process for producing the skeletal catalyst-coated thin metal structures of the present invention. In these embodiments, a six inch wide roll of nickel or other metal shim stock, for example, is coated by a slurry prepared by ball milling a mixture containing one or more metal powders or preformed bulk metal alloy powders that are precursors to catalytically active materials. It should be noted that the slurry always contains aluminum powder. The coated nickel roll stock is then introduced into a furnace under a reducing or inert atmosphere wherein at least one of the one or more metals in the slurry interdiffuses with the surface of the nickel roll stock forming an alloy or intermetallic that firmly binds the coating to the nickel substrate. Upon exiting the furnace, the coated metal substrate can be either formed into a desired shape or continue for additional processing before being formed into a desired shape.

Although FIG. 1 and the following disclosure is predominantly directed to the use of thin metal foil as the metal substrate, similar process steps would be used if the metal substrate was a flattened mat of metal fiber or a flattened woven metal fiber assembly.

In the embodiment where the coated metal substrate is a thin metal foil that is formed into a desired shape before any additional processing occurs, the coated metal stock is slit, optionally corrugated, chopped, and assembled upon leaving the furnace to form the desired catalyst structure. The desired catalyst structure may then be assembled into a larger structure, such as by arranging cut pieces and fastening them by methods known in the art to produce a stackable scaffold superstructure. Then, the coated metal pieces are leached in an aqueous caustic solution as a formed shape and subsequently subjected to a chelating acid bath such as a citric acid bath. Following the chelating acid bath, the coated metal pieces are passivated in a bath of a mild oxidant, preferably dilute hydrogen peroxide aqueous solution, and then water-washed and dried. After passivation, but prior to the drying step, formed catalyst structures optionally can be abraded with a high velocity jet of water to remove weakly adhered layers, if any, then dried. Finally, the formed catalyst structures can be packaged.

In another embodiment of the present invention, a conforming oxidic catalyst support layer is formed on the surfaces of the adhered alloy or intermetallic layer (i.e., the layer formed after the one or more metals in the coating slurry interdiffuses with the surface of the metal foil substrate). In this embodiment of the present invention, the intrinsic oxidic catalyst support layer is formed by adding an additional step to the disclosed process. That step involves heating the coated metal substrate (after the leaching step or in place of the leaching step) in an oxygen containing atmosphere (e.g., air) to form an adherent oxide coat (i.e., an intrinsic oxidic layer suitable as a catalyst support layer) directly, without application of an additional washcoat. The additional step preferably occurs in an air calcination unit after the gross form-factor fabrication step, if formed parts are desired. The topologies and specific surface areas of the oxidized surfaces are distinctly different depending on whether or not the leaching step is applied prior to the oxidation step. Thus, the need for inclusion of the leaching step is determined by the requirement for additional surface area or macroporosity in the finished catalyst support structure.

In the embodiment where the coated metal substrate is subjected to additional processing before being formed into a desired shape, the coated metal stock is subjected to a continuous leaching step in an aqueous caustic solution, before being subjected to a chelating acid bath. After the acid bath, the coated metal stock is subjected to continuous passivation by passage through a bath of dilute aqueous hydrogen peroxide solution for a time sufficient to quench any pyrophoricity. The coated metal stock may optionally be subjected to continuous abrasion using a high velocity jet of water (i.e., to cause abrasion of the outer surfaces) after being subjected to the acid bath and before or after the passivation step. After the passivation step, the coated metal stock is then rinsed with water and dried. Acetone rinsing can be used to accelerate drying, but care must be taken to prevent contact of acetone and hydrogen peroxide-containing solutions or residues to avoid formation of potentially explosive compounds. Following the drying step, the coated metal stock is slit, corrugated, and chopped into the desired catalytic elements for the form factor of interest. The desired catalyst elements may then be assembled into a larger scaffold structure, such as by combining (e.g., use of stacking and fastening by methods known in the art) the smaller catalyst elements. Finally, the formed catalytic scaffold structures can be packaged.

In another embodiment of the present invention, a conforming oxidic catalyst support layer is formed on the surfaces of the skeletal metal catalyst layer (including within the macro pores and cracks in the skeletal metal catalyst layer). In this embodiment of the present invention, the intrinsic oxidic support layer is formed by heating the passivated, leached metal substrate in an oxygen containing atmosphere (e.g., air) to form a thicker adherent oxide coat (i.e., an intrinsic catalyst support layer). The additional step preferably occurs in an air calcination unit after the scaffold gross form-factor fabrication step.

Regardless of whether the coated metal substrate is formed into a desirable shape before or after the additional processing steps, the leaching step is performed in a caustic solution, preferably a solution comprising NaOH. As is known in the art, the leaching step selectively removes some of the aluminum and certain aluminides from the coating, forming porosity in the coating, but leaving in place various other aluminide compounds. The temperature of the leaching bath is from about 65 to 95° C., preferably from about 80 to 90° C. The amount of time that the coated metal substrate spends in the leaching bath is from about 5 to 50 minutes, preferably from about 25 to 45 minutes.

The citric acid bath is only one embodiment of the present invention. Suitable acid baths would be those comprising, for example, a mineral acid or carboxylic acid, but polyprotic acids forming chelating anions are preferred The temperature of the acid bath is from about 20 to 40° C., preferably from about 25 to 30° C. The amount of time that the coated metal substrate is held in the acid bath is from about 2 to 10 minutes, preferably from about 3 to 5 minutes.

The use of the intrinsic oxidic catalyst support layer is desirable when very low loadings of precious or platinum metal compounds are necessary or desirable for catalysis or when complex molecular structures with bonded fragile ligands are required rather than bare zero-valent base metals. Deposit of such materials directly onto a reactive base metal substrate, in the absence of an inert oxidic layer, could displace ligands or bury the precious or platinum metal catalytic top layer as the metallic surface restructures with use. Furthermore, the chemical selectivity of the composite metal surface catalyst would be altered by the presence of the dominant reactive metal of the substrate. Thus, an intrinsic, catalytically inert oxidic catalyst support layer can act similarly to a ceramic washcoat layer known in the art to disperse such catalytic species without altering their site-specific activities.

Although lacking some of the advantages of a self-supported thin layer skeletal metal catalyst surface coating, the conforming oxidic catalyst support layer is well adhered to the underlying substrate. Moreover, the intrinsic oxidic catalyst support layer is straightforwardly produced after the gross-form fabrication step so as not to be damaged by mechanical processing. Once impregnated with active catalyst species, the uniform thickness of the intrinsic oxidic catalyst support layer also promotes uniform temperature distribution to reduce the probability of damage from localized hot spots when structured catalysts are used to promote exothermic reactions such as the initiation of catalytic combustion of organic vapors in an oxygen-rich gas.

In another embodiment of the present invention, catalyst alloy compositions have been created according to the disclosed methods that are highly active and hydrothermally stable. The alloy compositions were prepared using nickel foil substrates. The catalyst series investigated on nickel substrates is based on compositions chosen using two-part, three-level partial factorial designed experiments that were pre-planned to screen initial suitability for ternary alloys of nickel, aluminum, and a refractory metal. One of the refractory metals selected was zirconium. Pre-alloyed nickel-zirconium powders were used in some cases. The other refractory metals in the screening experiments were selected based on three criteria: having an elemental melting point significantly greater than nickel, having the ability to form a ternary aluminide with nickel at a relatively low temperature, and having a relative bulk cost lower than that of zirconium.

The other refractory metals (i.e., other than zirconium) selected were nickel (control), vanadium, chromium, titanium, tungsten, niobium, molybdenum, and tantalum. Replicates of each catalyst were prepared by coating the nickel foil substrates with slurries that (when dried) contained the refractory metal at nominally 0, 5, and 11 weight percent loading (i.e., based on the weight of all of the metals in the applied slurry) for screening purposes. After the furnacing step, all formulations were judged to be pliable and durable enough for mechanical corrugation and formation into honeycombs except several containing titanium. Modified compositions of the titanium catalysts that contained slightly lower aluminum content were found to be acceptably pliable and durable towards bending and corrugation directly after the furnacing step. Screening of the metal supported catalyst containing the various alloy compositions was performed to determine fitness-for-use. Screening included analysis of: (1) relative activity in a low pressure hydrocarbon reforming reaction conducted in a quartz microreactor under a particular set of conditions; and (2) BET surface area retention after steam deactivation to measure extent of sintering. Table 1 shows the initial conversion (i.e., percent conversion of total carbon atoms in the reactant feed per total geometric area in $cm^2$ of the catalyst) for mixed light hydrocarbon reforming (in a laboratory reactor) for catalysts prepared according to the disclosed process.

TABLE 1

| Catalyst | Coating Compositions | Initial Conversion per geometric area For Ni-only and Ni alloy catalysts |
| --- | --- | --- |
| Ni-shim | No Coating | 0.57 |
| Al—Ni—Ni only | Al(59.4%)—Ni(39.6%)—B(1%) | 0.87 |
| Ni—Zr-11% | Al(52%)—Ni(36%)—Zr(11%)—B(1%) | 1.50 |
| Ni—Cr-11% | Al(52%)—Ni(36%)—Cr(11%)—B(1%) | 1.61 |
| Ni—Ti-11% | Al(52%)—Ni(36%)—Ti(11%)—B(1%) | 1.54 |
| Ni—V-11% | Al(52%)—Ni(36%)—V(11%)—B(1%) | 1.27 |
| Ni—Ta-11% | Al(52%)—Ni(36%)—Ta(11%)—B(1%) | 1.45 |
| Ni—Zr-5% | Al(56%)—Ni(38%)—Zr(5%)—B(1%) | 1.63 |
| Ni—Cr-5% | Al(56%)—Ni(38%)—Cr(5%)—B(1%) | 1.41 |
| Ni—Ti-5% | Al(56%)—Ni(38%)—Ti(5%)—B(1%) | 1.23 |
| Ni—V-5% | Al(56%)—Ni(38%)—V(5%)—B(1%) | 1.38 |
| Ni—Ta-5% | Al(56%)—Ni(38%)—Ta(5%)—B(1%) | 1.24 |

Table 2 (below) shows the BET surface area before and after steam deactivation. Because both initial activity and resistance to deactivation are important for optimal performance, Ni—Zr and Ni—Cr alloys and higher loading of Ni—Ta are preferred compositions. The remaining multimetallic alloy catalysts also perform better than non-alloyed foraminous nickel compositions or compositions with added nickel plus aluminum only on the nickel substrate. The first entry in Table 2 was prepared by coating a nickel substrate with only aluminum as the metallic component of the coating slurry. The last entry in Table 2 was prepared by adding only aluminum, boron and nickel to the coating slurry but no other metallic components.

TABLE 2

BET Surface Area Analysis of Multimetallic Alloy Catalyst Coatings (not passivated)

| Coating compositions | Surface Area Before Steaming[1] | Surface Area After Steaming[2] |
|---|---|---|
| Al(58.7%)—Ni (40.3%)—B(1%) | 83 | 5 |
| Al(52%)—Ni(36%)—Zr(11%)—B(1%) (RG-49-78) | 152 | 26 |
| Al(52%)—Ni(36%)—Zr(11%)—B(1%) | 153 | 29 |
| Al(52%)—Ni(36%)—Cr(11%)—B(1%) | 100 | 21 |
| Al(52%)—Ni(36%)—Ti(11%)—B(1%) | 75 | 9 |
| Al(52%)—Ni(36%)—V(11%)—B(1%) | 156 | 31 |
| Al(52%)—Ni(36%)—Ta(11%)—B(1%) | 132 | 25 |
| Al(56%)—Ni(38%)—Zr(5%)—B(1%) | 158 | 27 |
| Al(56%)—Ni(38%)—Cr(5%)—B(1%) | 175 | 20 |
| Al(56%)—Ni(38%)—V(5%)—B(1%) | 151 | 30 |
| Al(56%)—Ni(38%)—Ta(5%)—B(1%) | 146 | 24 |
| Al(59.4%)—Ni(39.6%)—B(1%) | 133 | 19 |

[1]Surface Area measured by BET ($m^2$/g coating). All values are average of values obtained for two batches of samples except for RG-49-78.
[2]Surface Area measured by BET ($m^2$/g coating). All values are single values from one batch.

Additional independent characterization experiments were conducted to further differentiate the multimetallic formulations of this invention from those that did not include refractory alloy metals and from a commercial methane steam reforming catalyst comprising a nickel oxide on a ceramic support. Accordingly, passivated catalysts were reduced in situ prior to measuring their hydrogen chemisorption capacities by a flood adsorption/temperature programmed desorption method, a method known in the art. These data were compared to similar measurements on ground and sized commercial nickel-based ceramic catalyst pellets (Hi-Fuel 110, Alfa-Aesar Johnson-Matthey Co.). Standard algorithms in commercial software that account for differences in metal loading were used to estimate dispersions and metal areas derived from the hydrogen chemisorption data obtained. As shown in Table 3, replacing nickel with either 11% (by weight) zirconium or chromium resulted in increased hydrogen binding capacity, which translates to greater apparent dispersion, and in greater exposed metal area, directionally consistent with earlier BET measurements. The specific surface areas and dispersions of nickel computed for fresh (passivated) multimetallic catalysts of this invention are slightly higher than those areas measured for fresh Hi-Fuel-110 commercial catalyst after similar pre-reduction.

TABLE 3

Apparent Dispersion Measured by a Hydrogen Flood Adsorption/Temperature Programmed Desorption Method After a Temperature Programmed Reduction Step

| Catalyst Sample | Composition of Original Coating | Average Apparent % Dispersion after TPR (assume 0.5 stoichiometry for all coated metal content) |
|---|---|---|
| Hi-Fuel-110 (Alfa-Aesar) | Unknown | 7.8 |
| ZrNi passivated | Al(52%)—Ni(36%)—Zr(11%)—B(1%) | 12.0 |
| ZrNi steamed | Al(52%)—Ni(36%)—Zr(11%)—B(1%) | 2.5 |
| CrNi passivated | Al(52%)—Ni(36%)—Cr(11%)—B(1%) | 10.3 |
| CrNi steamed | Al(52%)—Ni(36%)—Cr(11%)—B(1%) | 1.7 |
| Ni only passivated | Al(59.4%)—Ni(39.6%)—B(1%) | 8.4 |
| Ni only steamed | Al(59.4%)—Ni(39.6%)—B(1%) | 2.3 |

EXAMPLE 1

An 11% Zr—Ni multimetallic catalyst (designated as RG-49-78) was prepared as described below. First, a 900 mL slurry containing 611 g of Al powder (10 micron average particle size), 109.1 g of Ni powder (Conductive Nickel Pigment type 525 D, -250 mesh obtained from Novamet), 444.3 g of Zr/Ni alloy (30/70; obtained from Chemetall), 10.1 g boron powder (elemental amorphous boron 95%; 0.5 to 3 microns; obtained from CR supply), 20.9 g of methyl methacrylate based binder, and 397.1 g of acetone were milled in a ball mill for about 12 hours with 150 mL of ¼ inch steel balls. The resultant slurry was then applied by dip coating to a Ni shim stock substrate (nominally 2 mil thick) that had been pre-cleaned with acetone and the resulting slurry coating thickness ranged from 5.75 to 6.25 mil. After drying in a hot air stream, the coated substrate was passed through a four foot long furnace fitted with an open-ended retort at a speed of 12 ft/min. The temperature in the furnace was 750° C. and the atmosphere was hydrogen gas (the hydrogen gas flow rate to the furnace was 200 SCFH). After exiting the furnace, the coated substrate was leached in a 200-225° F. aqueous solution containing 25% NaOH for 45 minutes and then rinsed with water. The coated substrate was then bathed in a citric acid solution (5% by weight citric acid in water) for 3 minutes and then again rinsed with water. The coated substrate was then passivated by immersion in an aqueous solution containing 3% (by weight) $H_2O_2$ for 12 minutes and subsequently rinsed with water again. Finally, the coated substrate was rinsed with acetone and dried with nitrogen gas.

The catalyst demonstrated an initial (passivated) surface area of 151 $m^2$/(g-coating), and aliquots were subjected to successive steaming periods or to successive periods of attrition using a high pressure water jet. Durability was judged by monitoring weight loss versus attrition time (see Table 4 below) and versus jet pressure and by monitoring SEM thickness measurement after cross sectional polishing (see Table 5 below). Weight loss and surface area measurement were also made after successive periods of steaming at 900° C.

TABLE 4

Weight Losses of a Zr—Ni Catalyst After Successive Periods of Steaming or Water Jet Abrasion

| Steaming of RG-49-78 at 900° C. | | High Pressure Water Jet RG-49-78 (about 1880 psi at max nozzle setting) | |
|---|---|---|---|
| Treatment Time (hr) | % Weight Loss | Treatment Time (sec) | % Weight Loss |
| 2 | 4.04 | 30 | 9.93 |
| 3 | 5.36 | 150 | 10.27 |
| 6 | 3.13 | 300 | 8.74 |
| 9 | 3.76 | — | — |

TABLE 5

SEM Coating Thickness Measurements of Distinct Layers in Fresh, Steam-Aged and Used Catalysts

| Sample | Inner Coating (By SEM) (μm) | Total Coating (one side-by SEM) (μm) |
|---|---|---|
| RG-49-78 Fresh | 7.5 ± 1.6 | 45.8 ± 7.3 |
| RG-49-78 Steamed at 900° C. for 9 hours | 7.4 ± 1.3 | 28.1 ± 7.0 |
| RG-49-78 Used | 10.1 ± 2.0 | 33.6 ± 6.8 |

Successive abrasion of the catalyst resulted in an initial weight loss of the friable material that leveled out after an 8-9% by weight loss. Steaming for various periods up to 9 hours results in smaller weight losses that did not continue to increase after the initial loss. Scanning electron microscope (SEM) measurement of the polished cross sections strongly supports the conclusion that initial attrition is due to loss of a relatively loosely bound outer surface layer, but that no or little loss occurs in the highly active inner core that appears to be the diffusion layer, which is firmly affixed to the metal substrate.

Figure 2B:
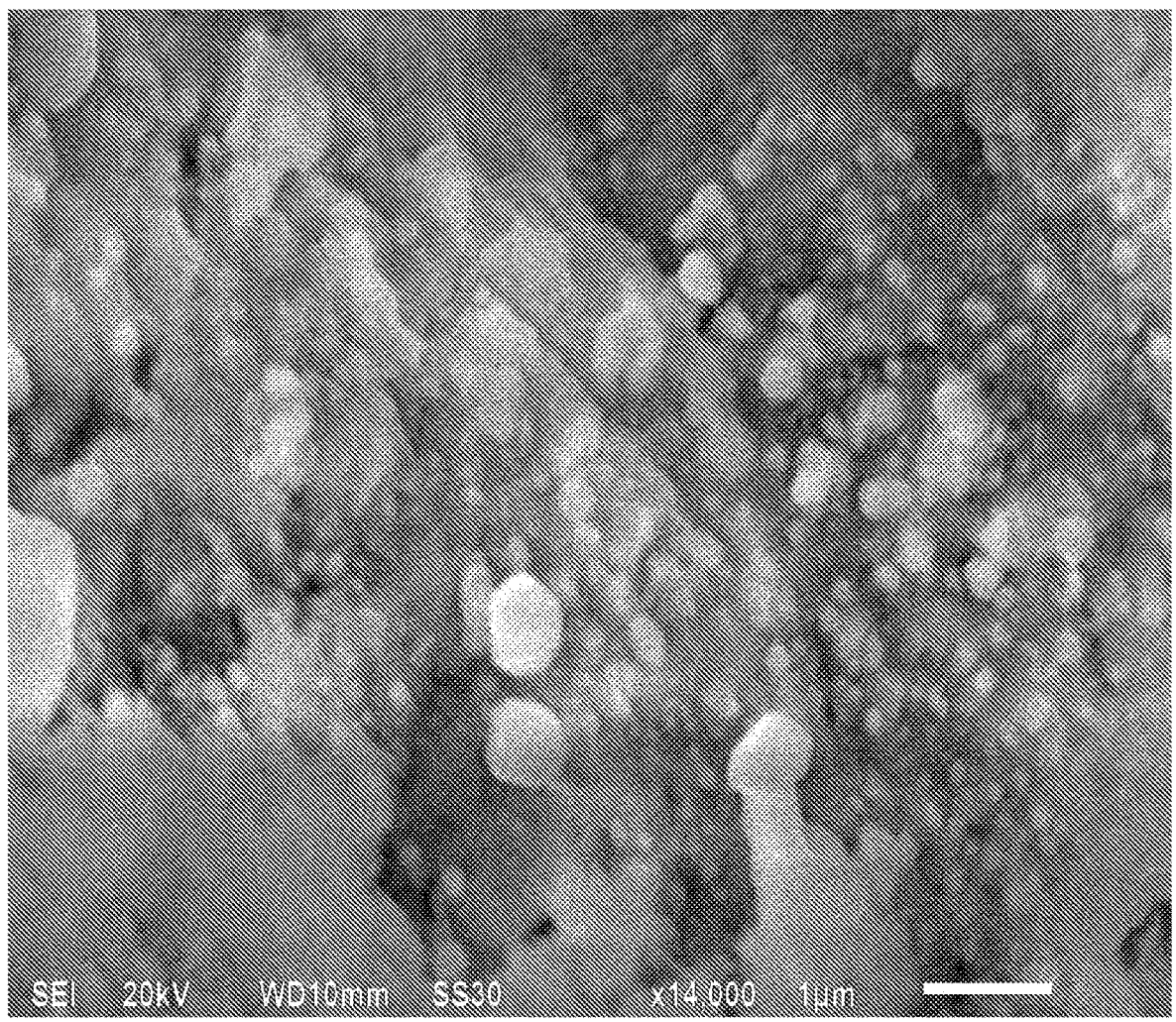
Figure 2C:
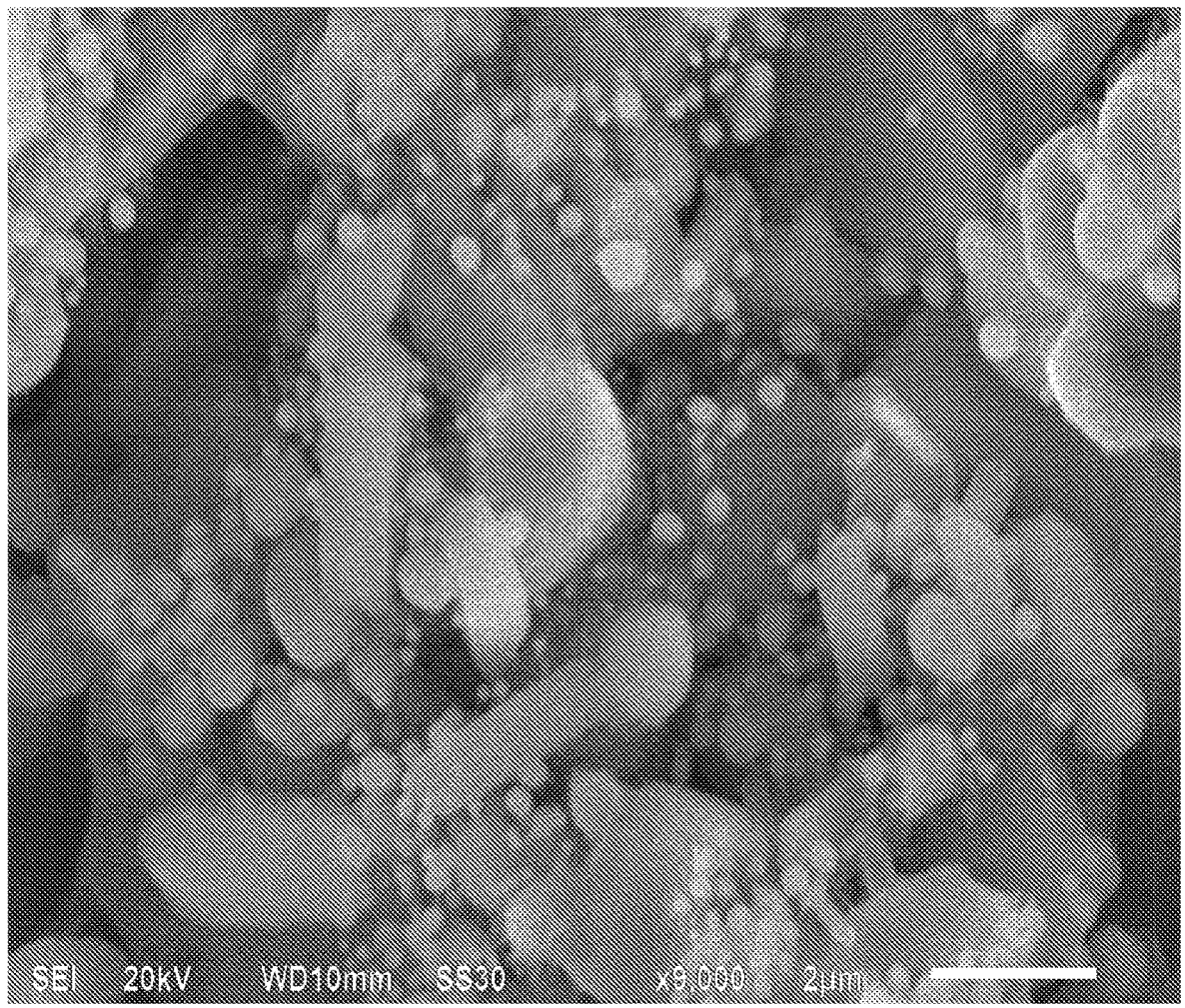

Table 6 (below) shows the relative initial hydrocarbon reforming activity (i.e., percent conversion of total carbon atoms in the reactant feed per total geometric area in $cm^2$ of the catalyst) of the same catalyst type (identified as RG-49-78) after attrition and shows BET surface areas before and after steaming. The inner core, exposed after attrition, is just as or more active than the fresh catalyst within experimental error. Thus, the catalyst is shown to remain stable and extremely active after an initial loss of outer layer. Moreover, deactivation does not progress linearly with continuing time of exposure to highly abrasive conditions or to conditions that facilitate rapid sintering. Further, no detectable phase change (determined from DTA/TGA data) exists at high temperature after the initial reduction of the passivation oxide. Reduction of the oxide accounts for a large portion of the weight loss observed on stream. FIGS. 2A, 2B and 2C show the effectiveness of steaming at simulating the sintering encountered during aging of the catalyst on-stream as evidenced by the loss of sharp edges of crystallites and formation of spherical structures in similar fashion.

Also, as shown in Table 6, the BET surface areas of the resulting materials are similar after steaming and after extended exposure to process conditions.

TABLE 6

Initial Light-Hydrocarbon Reforming Activity After Increasing Periods of Catalyst Attrition, and BET Surface Areas After Increasing Periods of Steaming Compared to Used Catalyst

| Sample | Treatment Time | Xc/geometric area | BET SA Passivated ($m^2$/g coating) | BET SA Passivated-Steamed ($m^2$/g coating) |
|---|---|---|---|---|
| RG-49-78 (previous batch) Reference | 0 sec | 1.40 | — | — |
| RG-49-78 (pressure washed) | 30 sec | 1.21 | — | — |
| RG-49-78 (pressure washed) | 300 sec | 1.52 | — | — |
| RG-49-78 (previous batch) Reference | 2 hr | — | 147 | 16 |
| RG-49-78 (steamed at 900° C.) | 6 hr | — | — | 14 |
| RG-49-78 (steamed at 900° C.) | 9 hr | — | — | 15 |
| RG-49-78 Used | — | — | — | 14 |

EXAMPLE 2

An experiment was run where an 11% Zr/Ni/Al/B/Ni catalyst was prepared for use in a steam methane reforming reaction, according to an embodiment of the methods disclosed in the present invention. First, a 900 mL slurry containing 611.0 g of Al powder (10 micron average particle size), 109.1 g of Ni powder (Conductive Nickel Pigment type 525 D, −250 mesh obtained from Novamet), 444.3 g of Zr/Ni alloy (30/70; obtained from Chemetall), 10.1 g of boron powder (elemental amorphous boron 95%; 0.5 to 3 microns; obtained from CR supply), 20.9 g of methyl methacrylate based binder, and 397.1 g of acetone were milled in a ball mill for about 12 hours with 150 mL of ¼ inch steel balls. The resultant slurry was then applied by dip coating to a Ni shim stock substrate (nominally 2 mil thick) that had been pre-cleaned with acetone and the resulting slurry coating thickness ranged from 5.75 to 6.25 mil. After drying in a hot air stream, the coated substrate was passed through a four foot long furnace fitted with an open-ended retort at a speed of 12 ft/min. The temperature in the furnace was 900° C. and the atmosphere was hydrogen gas (the hydrogen gas flow rate to the retort was 200 SCFH). After exiting the furnace, the coated substrate was leached in a 200-225° F. aqueous solution containing 25% NaOH for 45 minutes and then rinsed with water. The coated substrate was then bathed in a citric acid solution (5% by weight citric acid in water) for 3 minutes and then again rinsed with water. The coated substrate was then passivated by immersion in an aqueous solution containing 3% (by weight) $H_2O_2$ for 12 minutes and subsequently rinsed with water again. After the $H_2O_2$ treatment, the coated substrate was then abraded with a high velocity jet of water at 1880 psi for 2 minutes on each side with the coated substrate fixed at 3 inches distance from the nozzle of the water jet. The water jet abrasion caused the coated substrate to lose approximately 3.9% of its mass. Finally, the coated substrate was rinsed with acetone and dried with nitrogen gas and then passivated by immersion in an aqueous solution containing 3% (by weight) $H_2O_2$ for 12 minutes and subsequently rinsed with water again then dried in air.

EXAMPLE 3

Scanning electron microscope images (SEM) were taken of fresh, steamed and used catalytic foils derived from the same preparative batch described in Example 2. The used samples had been exposed to SMR process conditions for several hundred hours prior to imaging. In the images, the outer layer appears less prominent and highly diminished in thickness with aging. The inner core however remains adhered and highly reactive either after the steam treatment or after being used under process conditions for several hundred hours.

EXAMPLE 4

A sample of zirconium-nickel foil composition, prepared according to the method described in Example 2, that had been furnaced at 900° C. under hydrogen, anaerobically leached, citric acid treated, passivated and pre-attrited using a high pressure water jet, and then dried, was tested for steam methane reforming performance. In a packed-bed plug-flow integral conversion reactor, operating under commercially viable steam methane reforming conditions, instantaneous on-line analytical measurements of product composition and corresponding temperature differentials between applied temperature at the reactor wall and the catalyst surface were used to compute activity versus time. Bulk heat and mass transfer effects on activity that could be attributable to form factor differences were excluded in these tests by using similarly sized foil slivers embedded in inert packing rather than using monolithic form factors. However, intraparticle (molecular scale) mass transfer effects, dependent on the surface nanostructures of the foils, still could influence relative performance.

In this test, the catalyst foil not only generated higher volumetric activity than the reference catalyst, a ceramic-supported nickel oxide of a type used commercially, but also survived 900 hours without deactivation or significant physical degradation.

The following examples demonstrate the effectiveness of the coated foils or fibers of the present invention to act as catalyst supports for promoted precious or platinum group metal catalysts. The substrate metal used to produce these catalysts was 430 grade stainless steel (a well-known alloy that contains no significant amounts of aluminum or yttrium). The 430 grade stainless steel alloy is a preferred metal substrate material for the catalysts of the present invention, especially when those catalysts need to be resistant to high temperatures (e.g., temperatures in the range of 800 to 1,000° C.).

EXAMPLE 5

Preparation of Catalyst Supports 430 alloy grade stainless steel foil shim stock, 2 mil thick, was obtained from Ulbrich Co. of North Haven, Conn., USA as 4 inch wide pieces. These were cut into flat strips measuring approximately 1.5 inch by 8 inch and washed with acetone. Each of several strips was coated with a slurry using a laboratory-scale falling-film "dip coater" then dried by hanging in a heated air stream. The coating slurry was composed as follows:
aluminum powder (about 3 μm average particle size): 57.8 wt %
methyl acrylate based binder: 4.2 wt %
Acetone: balance After drying, the coated strips were stapled to leaders of metal foil and passed through a 4 foot long retort housed in a clam shell furnace held at 730° C. at 6 feet per minute under flowing hydrogen, then cooled in air. The coating appeared uniform and adherent at this point. The "hydrogen furnaced" intermediates were placed in a box furnace on a ceramic fixture that allowed air circulation on both sides of the foil strips and were heated in static air with the following schedule: room temperature to 650° C. ramped at 20°/min then held at 650° C. for 1.5 hours. The samples were allowed to cool in the box furnace over about 1.5 additional hours. The resulting oxidized strips were flexible, with the coating remaining intact after flexure.

EXAMPLE 6

Catalyst Preparation A: Ce/Cu/Pd/Pt Catalyst

Support strips that were prepared as described in Example 5 were cut into smaller pieces of 25 by 80 mm dimensions and impregnated with catalytic agents as described below. Ammonium hexanitrocerate (IV), $(NH_4)_2Ce(NO_3)_6$ (0.3958 g), and copper (II) acetate hydrate (0.0262 g) were dissolved into 0.5 mL of distilled water with sonication, then acetonitrile (0.11 g) was added to form a lime green solution. The support strip was placed on a watch glass and wet with the Ce—Cu solution on both sides. Excess solution was tapped off the metal strip back onto the watch glass, then the wet strip was dried for several minutes in a hot air stream. After drying, the sequence of impregnation and drying was repeated two more times until the solution had been depleted. The dried strip was calcined in a static box furnace in ambient air and heated by ramping at 20° C./minute to 500° C., then held at this temperature for 30 minutes and then cooled. The cooled strip was lightly wiped with a laboratory tissue then blown clean with a compressed air nozzle to remove a small quantity of loose powder from the surface. The strip then was impregnated with palladium and platinum salts as described below. Dichlorotetraaminepalladium (II) monohydrate, $Pd(NH_3)_4 (Cl)_2 \cdot H_2O$ (0.0766 g) and tetraamineplatinum (II) nitrate, $Pt(NH_3)_4 (NO_3)_2$ (0.0367 g) were dissolved into 0.5 mL of distilled water without pH adjustment. The strip was wet with the Pd/Pt solution as described above, then the strip was dried in a hot air stream. The wetting/drying sequence was repeated carefully until the entire quantity of solution had been consumed. The dried strip was calcined in a box furnace in air by heating at 20° C./min to 500° C., then held at 500° C. for 2 hours and then cooled slowly in the furnace. The sample was lightly wiped with laboratory tissue then blown clean with compressed air. Weight measurement showed that the sample had gained weight in the coating-calcining-wiping process. Based on the assumptions of retention of applied molar ratios, the composition of expected reaction product phases, and the actual final weight gain, the nominal catalyst composition was computed as 5.56% $CeO_2$, 0.51% CuO, 0.828% Pt, and 1.59% PdO.

EXAMPLE 7

Catalyst Preparation B: Ce/Pd/Pt Catalyst

A second catalyst was prepared as above (i.e., as described in Examples 5 and 6), except the copper salt and acetonitrile components were excluded from the formulation, only one calcination step was included, and the following quantities of precursor materials were used for a similarly sized support strip:

| | |
|---|---|
| $(NH_4)_2Ce(NO_3)_6$ | 0.380 g |
| $Pt(NH_3)_4 (NO_3)_2$ | 0.030 g |
| $Pd(NH_3)_4 (Cl)_2 \cdot H_2O$ | 0.075 g |

EXAMPLE 8

Catalyst Preparation C: Pd/Pt Catalyst

A third catalyst was prepared as above (i.e., as described in Examples 5, 6 and 7), except both the cerium and copper salts and the acetonitrile components were excluded from the formulation, only one calcination step was included, and the following quantities of precursor materials were used for a similarly sized support strip:

| | |
|---|---|
| $Pt(NH_3)_4 (NO_3)_2$ | 0.028 g |
| $Pd(NH_3)_4 (Cl)_2 \cdot H_2O$ | 0.074 g |

Catalyst Testing for Oxygen Depletion

Each of the three catalysts described above (i.e., A, B and C), were tested in a laboratory scale oxygen depletion reactor screening test to determine their relative "light off" temperature performance. The test is conducted by passing a precise flow rate of a particular gaseous reactant solution containing a hydrocarbon (heptane) and oxygen over a fixed size of coiled, corrugated catalytic foil. Oxygen is the limiting reagent. As the temperature is ramped upwards at a precisely controlled rate, the product stream is continually analyzed for residual oxygen content. The isokinetic temperature (i.e., corrected for the time delay of transport between the reactor and the analyzer) at which point 50 mol % conversion of oxygen has occurred, termed $T_{50}$, is noted and used as a comparative measure of "light off" performance. Other features of importance are the initiation temperature and the shape and slope of the extinction curves (mathematically related to catalytic reaction rate) relative to those observed over other catalysts. Reaction rate data are normalized to reactor bed volume and to total exposed geometric surface area of catalytic foil. The test conditions used are described in Table 7 (below).

TABLE 7

| | |
|---|---|
| Catalyst size/form | coiled, corrugated foil of 25 by 80 mm dimensions before corrugation |
| Catalyst geometric area | 40 $cm^2$ |
| Feed composition | $O_2$: 1.1%; n-$C_7H_{16}$: 21.15%; Ar: 27.19% (internal standard); $N_2$: balance |
| T ramp | 7° C./min; 25 to 370° C. (typical) |
| $GHSV^1$ (based on total reactor vol) | ~8400 $h^{-1}$ |
| Hourly Face Velocity (based on actual area on both sides of catalyst) | 275.9 cm/h |
| Reaction overall stoichiometry | $C_7H_{16} + 11\ O_2 \rightarrow 7\ CO_2 + 8\ H_2O$ |
| Static pressure | Barometric |
| Analytical | quadrupole mass spectral analysis of $O_2$ partial pressure at m/e = 32.0 |

[1] The GHSV (gas-hourly-space-velocity) was calculated at 25° C. and 760 torr. The reactor volume is computed as if it were a fully filled cylinder with no void volume between portions of catalyst.

Catalysts often equilibrate with repeated use as the Pt/Pd species on the surface adjust oxidation state ratios (reduce or oxidize) to achieve a steady-state condition. In this test, changes occur over 2-3 runs during which time their $T_{50}$ values typically move to lower values and their curve shapes become more symmetrical and often steeper in extinction of oxygen (catalysts get better). When time permits, the third run over each catalyst usually is taken as the definitive result for that particular composition in our laboratory.

Figure 3:
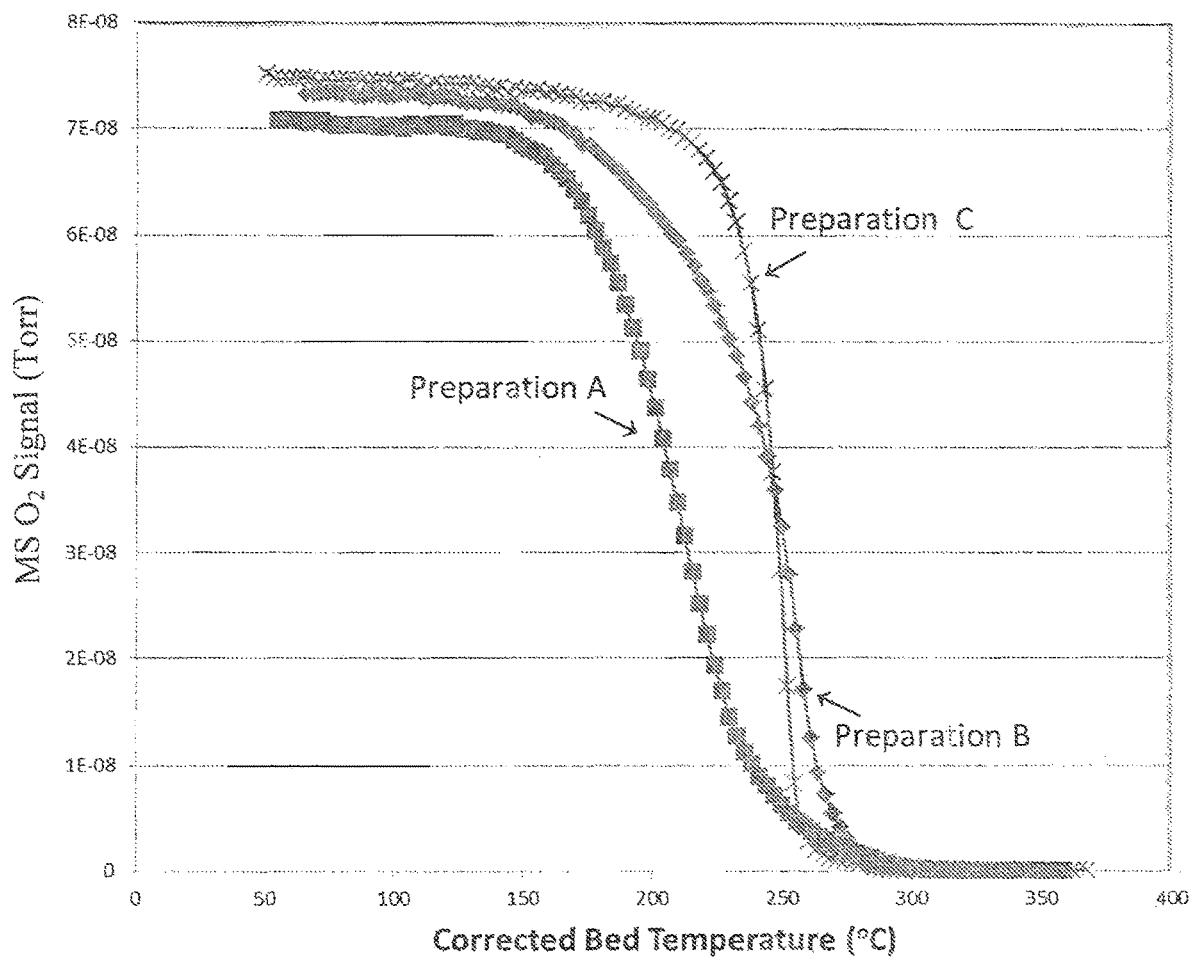
FIG. 3 is a graph showing the oxygen depletion in a light-off test of n-heptane over a platinum group metal catalyst prepared on a corrugated catalyst support foil of the present invention.

Table 8 (below) and FIG. 3 summarize the corrected data for the catalysts prepared as described above in Examples 6, 7, and 8. In FIG. 3, the y-axis values represent the $O_2$ partial pressure (in torr) measured by a mass spectrometer (i.e., determined from the $O_2$ signal at m/e=32). The x-axis values are the corrected catalyst temperature (i.e., isokinetic temperature; approximately two degrees celsius lower than measured temperature at catalyst bed) in degrees celsius".

Note that addition of cerium lowers the temperature at which the catalyst initiates the "light off" but does not affect the $T_{50}$ much. The co-addition of a copper component in addition to the cerium promotes an even lower temperature for initiation of the reaction and dramatically reduces $T_{50}$ as well. Table 8 (below) summarizes the quantitative data:

TABLE 8

| Example | Run | $T_{50}$ (° C.) (lower is better) |
|---|---|---|
| 6 - Catalyst Preparation A [Ce/Cu/Pd/Pt] | 1 | 209 |
| 7 - Catalyst Preparation B [Ce/Pd/Pt] | 3 | 245 |
| 8 - Catalyst Preparation C [Pd/Pt] | 3 | 247 |

Fibrous Material Embodiment

In a preferred embodiment of the present invention, thin metal fibers, such as thin 430 stainless steel fibers, are used as the starting material upon which aluminide and aluminum oxide layers are formed to create a fibrous material that functions as an effective catalyst support for platinum group or other metals. After impregnation with catalytic agents, this catalytic fibrous material (which can withstand high temperatures, for example from 600-900° C.) can be used in soot traps for diesel engines or in catalytic converters. For example, the catalytic fibrous material (e.g., containing a PGM catalyst) can be used to create a self-oxidizing partial diesel particulate filter (i.e., a partial diesel particulate filter conforms to the requirement for soot trapping efficiency of greater than 50% but less than 80%) featuring partial bypass of flow to ensure even loading of soot and to reduce pressure drop.

Catalytic soot traps filter carbonaceous soot particles from exhaust streams under rich combustion conditions and ignite and burn off the soot under lean combustion conditions via catalytic initiation of oxidation.

Most catalytic soot trap devices comprise a refractory oxide particle layer that is applied directly to a ceramic or metallic substrate before the catalytic species is applied. The refractory oxide particle layer is commonly referred to as a "washcoat," and its application is followed by application of the PGM components. The washcoat typically comprises high surface area oxides, such as, for example, transition-phase aluminum oxides, that stabilize and disperse the catalytic components (i.e., they maintain the specific surface area of the catalytic components under process conditions, without becoming volatile or detrimental to the catalytic species). The PGM, or other catalytic components, can then be applied in a second impregnation step over the cured washcoat layer, or can be added directly to the slurry of the washcoat particles (and adsorbed thereon) prior to coating of the metallic or ceramic substrate forms in a single coating step. The washcoat components may also comprise hydroxide precursors that cross-link during curing to form oligomers characterized by bridging oxygen groups. While the cross-linking improves adherence to the substrate, the washcoat is not directly covalently bonded to the metallic substrate.

Regardless of the specific composition, high solids content viscous slurries of washcoat materials are difficult to apply in uniform thickness over small formed openings or open channels that are part of the pre-shaped substrate structures. When metal supported catalysts are used to catalyze exothermic processes such as combustion, hot spots can arise if the washcoat, and the catalytic layer supported thereon, is not applied uniformly. Hot spots lead to accelerated failure of substrate materials as well as to deactivation of the catalytic components. Thus, uniform coating of substrate structures facilitates the production of durable catalytic devices.

In addition to challenges associated with application of the washcoat layer, the constituent materials used to prepare substrates (monoliths), whether ceramic or metallic, must be able to withstand severe processing conditions. These constituent materials must also be suitable for fabrication into form-factors that can trap soot without too high a pressure drop. The materials used to prepare substrates must also be compatible with the chosen washcoat layer to avoid delamination of this layer. Heat conduction, cost and corrosion-resistance in the presence of acidic gases such as sulfur oxides and steam are also important factors to consider when choosing substrate materials.

Metallic substrates are sometimes preferred over ceramic substrates because they can more easily be formed into complex shapes and/or because they are better at heat conduction. On the other hand, ceramics are sometimes preferred over metallic substrates due to the fact that many metals are easily corroded or destructively oxidized under severe process conditions. High alloy metals that are corrosion and oxidation resistant do find use as catalyst supports, but they are limited to high value added applications because of their high cost.

When metallic substrates are used, practitioners often employ high temperature stable alloys such as Fecralloy™. Due to its composition, Fecralloy™ generates, upon exposure to air, a thin aluminum oxide layer on the external surface of the metallic substrate that is protective against corrosion and oxidative degradation. The protective layer differs from washcoat oxide layers—which are designed to be porous—in that it is thinner and less pervious.

Unfortunately, fibrous forms of Fecralloy™ are expensive and difficult to work with. For example, some metal oxide washcoats adhere poorly to this alloy when applied by the usual slurry process without prior treatment of the surface. Many other metals such as corrosion-resistant high alloy steels can be used for high temperature applications, but these are extremely expensive or are too brittle to easily fabricate into coiled structures of appropriate fiber density needed for efficient small particle filtration.

Based on the aforementioned challenges, it would be desirable to provide a metallic material (and process for its production) for use as a catalyst substrate that exhibits good heat conduction, is corrosion resistant, is oxidation resistant, and provides for a uniformly distributed, and highly adherent, oxide layer. Such material should also be capable of being formed into a fibrous form factor (e.g., a monolith honeycomb; or a packed fiber body; or parallel plates) that is suitable for coating with platinum group metal catalytic components and that is suitable for fabrication into soot traps for diesel engines.

The catalytic soot trap embodiment of the present invention comprises a fibrous material comprising a highly adherent aluminum oxide outer layer of substantially uniform thickness. The aluminum oxide outer layer of the fibrous material acts as an intrinsic support for catalytic moieties, such as platinum group metal (PGM) catalytic moieties. The fibrous material of the instant invention is malleable enough to be fabricated into a low pressure-drop form factor, exhibits good heat conduction, is corrosion resistant and is resistant to oxidation. In addition to being used as a soot trap for diesel engines, the fibrous material (after the inclusion of the PGM) can also be used in catalytic converters.

In one aspect of the catalytic soot trap embodiment of the present invention, the fibrous material comprises a plurality of thin steel fibers comprising a chromium-iron alloy, an interdiffusion layer (also referred to herein as an aluminide layer) covering at least a portion of the surfaces of the plurality of thin steel fibers, and an aluminum oxide outer layer that adheres to, and interfaces with, the interdiffusion layer. The interdiffusion layer (also referred to herein as the aluminide layer) may comprise aluminum, substrate metal (here steel) and aluminides (i.e., intermetallics of aluminum and the substrate metal or metals contained in the substrate metal). In a preferred embodiment of the present invention, the aluminide layer covers most of the surface of the plurality of thin steel fibers and the aluminum oxide outer layer covers most of the surface of the aluminide layer.

The aluminum oxide outer layer has a substantially uniform thickness. In addition, this layer is sufficiently thick enough to act as a suitable support layer for catalytic moieties such as platinum group metal catalytic moieties and also provides protection against oxidation and corrosion. In a preferred embodiment of the present invention, the aluminum oxide outer layer is highly adherent to the aluminide layer.

The plurality of thin steel fibers is usually in the form of a pliable metal fiber bundle and comprises Type 430 or Type 434 steel. Furthermore, the plurality of thin steel fibers are typically able to retain ductility after being heated in air to temperatures of about 600° Celsius to about 900° Celsius.

The fibrous material of the present invention can be made by a method comprising the following steps:
(a) obtaining a plurality of thin steel fibers comprising a chromium-iron alloy;
(b) applying an aluminum coating onto the plurality of thin steel fibers;
(c) forming an aluminide layer by partially interdiffusing the aluminum from the aluminum coating into the surface of the plurality of thin steel fibers by heating in a diffusion furnace under an inert or reducing atmosphere; and
(d) forming an aluminum oxide outer layer (i.e., on the surface of the aluminide layer) having a substantially uniform thickness by subjecting the residual surface aluminum and aluminide layers to high temperature oxidation (e.g., in an oxidation furnace) in the presence of an oxidizing gas such as air.

The aluminum coating is typically formed from a slurry that comprises an aluminum powder and a binder. The aluminum coating can also comprise a stabilizer such as cerium oxide or other rare earth salts. The aluminum coating is usually applied to the plurality of thin steel fibers using a continuous falling film coater followed by a drying step.

The interdiffusion of the aluminum from the aluminum coating into the surface of the metal fibers takes place in a diffusion furnace at a temperature of from about 640 to 1,100° C., preferably from about 650 to 900° C., under a hydrogen atmosphere for a time of from about 0.2 to 4 minutes, preferably from about 0.3 to 1 minute.

The plurality of thin steel fibers containing an aluminide coating is usually heated in the oxidation furnace to a temperature of about 600° Celsius to about 950° Celsius for about 5 to about 120 minutes. In a preferred embodiment of the present invention, the aluminide coated fibers are heated in the oxidation furnace to a temperature of about 800° Celsius to about 950° Celsius for about 10 to about 15 minutes.

The fibrous material of the present invention can be made into a filter (e.g., a catalytic filter) by a method which includes performing steps (a) through (d) above and then steps (e) and (f) as described below:

(e) impregnating the plurality of thin steel fibers bearing the aluminide and aluminum oxide layers with a platinum group metal catalyst so as to infiltrate at least a portion of the aluminum oxide layer with the platinum group metal catalyst; and
(f) forming a filter from the fibrous material obtained from step (e).

Another method of making a filter according to the present invention comprises performing steps (a) to (d) as described above and then steps (e) and (f) as described below:
(e) forming a filter from the fibrous material obtained in step (d); and
(f) impregnating the filter obtained in step (e) with a platinum group metal catalyst so as to infiltrate at least a portion of the aluminum oxide layer with the platinum group metal catalyst, optionally followed by calcination.

The fibrous material comprising the aluminum oxide outer layer does not disintegrate (e.g., no delamination of the aluminum oxide coating) when subjected to substantial temperature changes, exhibits good heat conduction, is oxidatively stable (as measured by thermogravimetric analyzer (TGA), differential scanning calorimetry (DSC), and/or long temperature soaks in a heated air environment), and is not excessively brittle (i.e., it is malleable enough to be fabricated into a low pressure-drop form factor).

Experiments performed to measure the oxidative stability, measured by a thermogravimetric analysis (i.e., TGA), of two samples of fibrous materials showed that one of the samples (Sample 2), which was a coated fibrous material according to the instant disclosure, was more oxidatively stable in air at temperatures exceeding 1,000° Celsius than the other sample (i.e., Sample 1), which was an uncoated stainless steel fiber mat. Specifically, the two samples were tested for oxidative stability by heating the samples in flowing air (50 mL/min) from room temperature to 1,200° C. at a ramp rate of 20° C. per minute. In this oxidative stability experiment, the sample according to the present invention (i.e., Sample 2; a mat of thin steel fibers bearing a uniform aluminum oxide coating that is adhered to and interfaces with an aluminide layer) showed a weight gain just 1.4%, whereas the other sample (i.e., Sample 1; a mat of uncoated stainless steel, alloy 434, fibers) showed a weight gain of 9.2% under the same oxidation conditions. Sample 2 was made by the process described below.

A ¼ inch thick×2 inch wide 430 stainless steel fibrous mat (obtained from Ribbon Technology Corporation) was cut into strips measuring approximately 2 inch by 8 inch and those strips were cleaned with acetone. Each of the strips was coated with a slurry using a laboratory scale dip coater and then dried by hanging in a heated air stream. The coating slurry was composed of: (a) 58% by weight aluminum powder (about 3 micron average particle size); (b) 4% by weight methyl methacrylate (as a binder) and (c) 38% by weight acetone. After the drying step, the coated strips were stapled to leaders of metal foil and passed through (at six feet per minute) a four foot long retort housed in a clam furnace held at 710° C. The atmosphere in the furnace was flowing hydrogen. After emerging from the furnace, the samples were cooled in the ambient air. The hydrogen furnaced samples were then oxidized using a batch process wherein the samples were placed in a box furnace and heated in static air using the following oxidation conditions: room temperature to 630° C. ramped at about 5° C. per minute and then held at 630° C. for two hours before the temperature was ramped from 630° to 850° C. at about 2.4° C. per minute and held at 850° C. for two hours. The samples were then cooled to room temperature in ambient air. The resultant samples were flexible.

Figure 5:
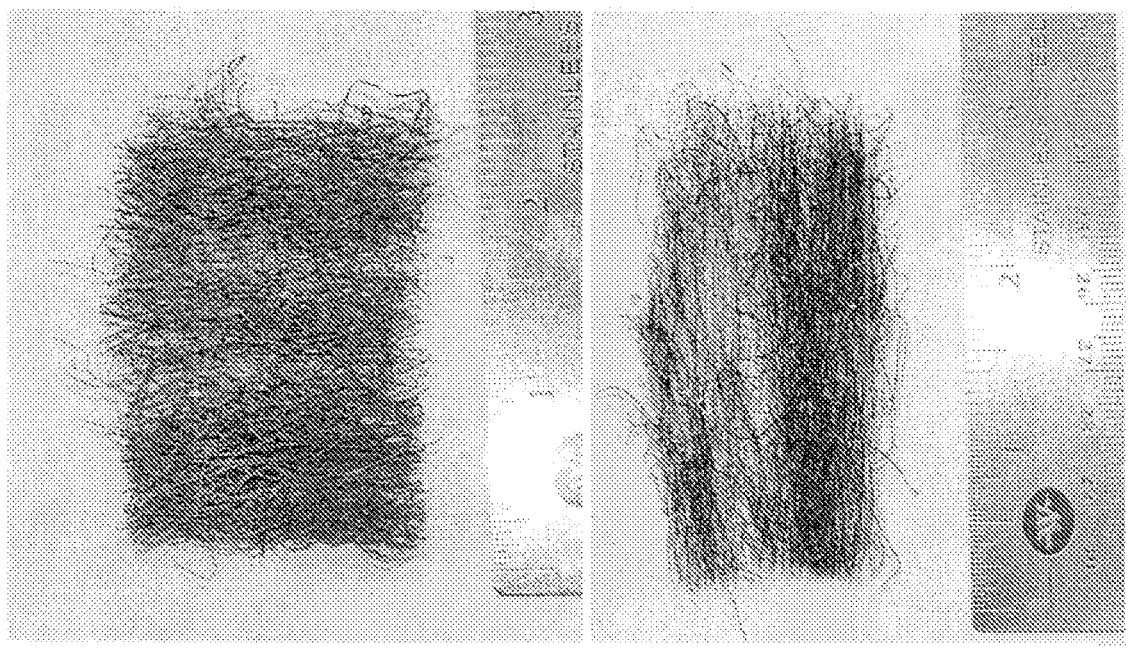
FIG. 5 is composed of two pictures of samples of the plurality of thin steel fibers that can be used to make the fibrous material of the present invention.

In a preferred embodiment of the present invention, the fibrous material of the instant disclosure is made by first obtaining coarse, medium, or fine grade 430 or 434 chromium-iron alloy stainless steel coiled mats of a suitable width and thickness, wherein each mat comprises a plurality of bundled thin steel fibers. FIG. 5 depicts two samples (ASC54-18-1 and ASC54-18-2) of the plurality of thin steel fibers (shaped into loose mats) that can be used to fabricate the fibrous material of the instant disclosure. The dimensions of these samples are shown below in Table 9.

TABLE 9

| Sample ID | Length (inches) | Width (inches) | Height (inches) | Volume (in$^3$) |
|---|---|---|---|---|
| A5C54-18-1 | 1.75 | 2.25 | 0.25 | 0.98 |
| A5C54-18-2 | 2.75 | 1.75 | 0.25 | 1.20 |

Figure 4A:
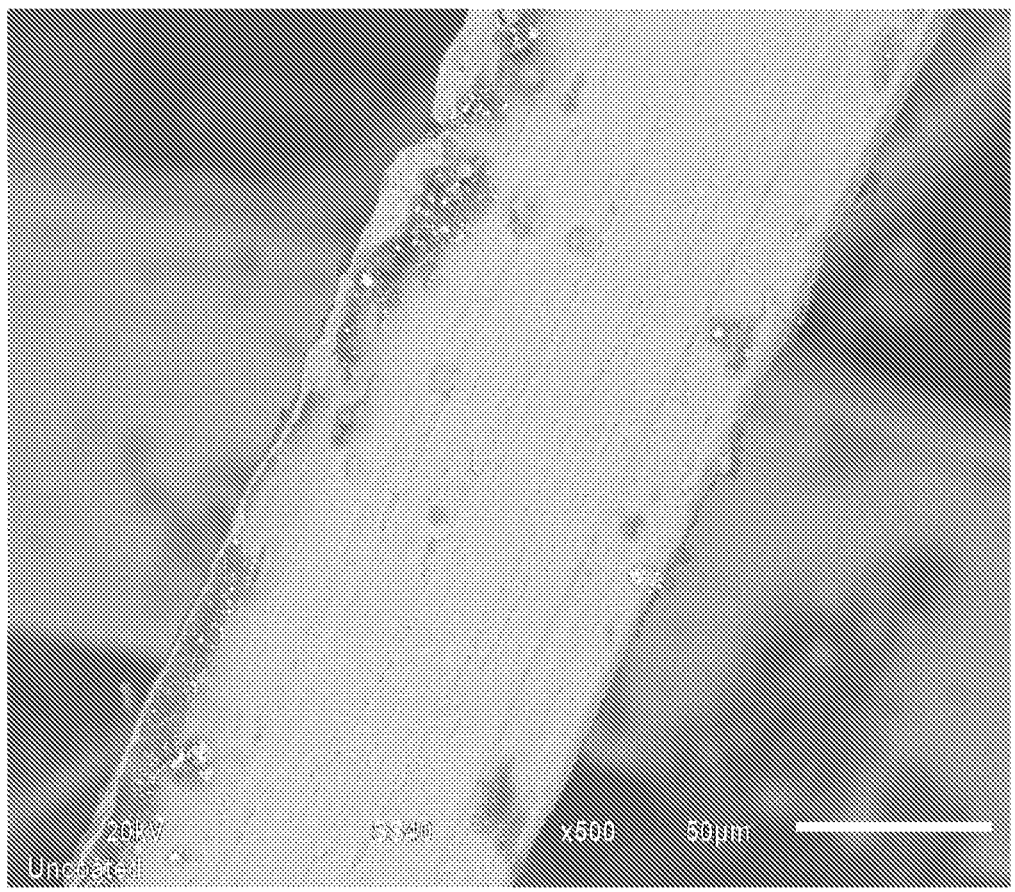
FIGS. 4A, 4B and 4C are scanning electron microscope images of the treated and untreated fibers used in Example 10.

In addition, FIG. 4A shows an SEM image of an individual thin steel fiber (i.e., untreated; as received) used to make the fibrous material of the present disclosure. The plurality of thin steel fibers comprises a chromium-iron alloy stainless steel that usually comprises about 14% to about 18% chromium. In addition, the mat of fibers is typically about ⅛ to about ½ inches thick and about 2 to about 4 inches wide, although wider mats of fibers can be used if desired.

Next, the plurality of thin steel fibers are coated with an aluminum coating. The aluminum coating is typically in the form of a slurry that comprises an aluminum powder, a binder (e.g., a methyl acrylate-type binder) and a solvent (e.g., acetone). The slurry may also comprise a stabilizing component such as cerium oxide or other rare earth salts. Usually, the slurry is ball milled with stainless steel balls overnight and is continuously stirred during the coating process.

Coating of the plurality of thin steel fibers with the aluminum coating is typically accomplished using the falling film method. The speed at which the plurality of thin steel fibers rise, and the length of the zone before the dryer, can both be adjusted according to skills known in the art to generate a substantially uniform coating of a desirable thickness.

After the aluminum coating has been applied, the plurality of thin steel fibers move vertically through a drying section to set the binder. Once the binder is set, the plurality of thin steel fibers are subjected to a diffusion furnace heated to a temperature of about 700 to about 760° C. for about 0.5 to about 4 minutes while continuously moving through a retort under a flowing hydrogen atmosphere. The steel fibers then emerge into air and are cooled for a sufficient time to bring them to room temperature. The diffusion furnacing allows the aluminum coating to partially diffuse into the plurality of steel fibers and form an aluminide layer. Without wishing to be bound by any theory, these partially diffused aluminide layers may contribute to corrosion resistance and adherence of the aluminum oxide outer layer formed during the oxidative furnacing step.

The method of the present embodiment of the instant invention does not require a liquid bath leaching step after reductive furnacing (i.e., the diffusion furnacing step) is completed. Therefore, once the steel fiber mats have been cooled, they are subjected to forming steps followed by oxidative furnacing or subjected directly to oxidative furnacing prior to any forming. The steel fiber mats are typically oxidatively furnaced for approximately 5 to 15 minutes. In addition, the oxidative furnace operates under flowing air and is usually heated to a temperature of about 600° Celsius to about 950° Celsius. More typically, the oxidative furnace is heated to a maximum temperature of about 650° Celsius to about 850° Celsius. If the fiber mat is formed into a shaped body after diffusion furnacing and prior to oxidation furnacing, the fully shaped body (i.e., in finished form) is placed into a static furnace for oxidative treatment in air.

Figure 4B:
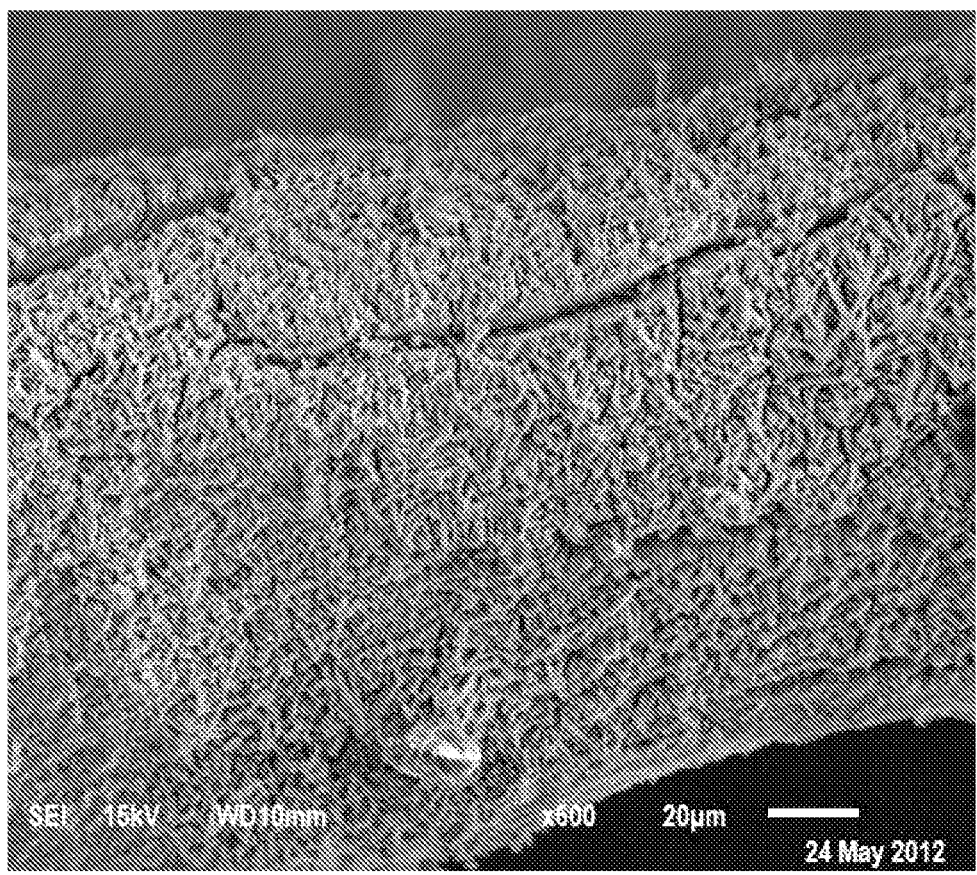
Figure 4C:
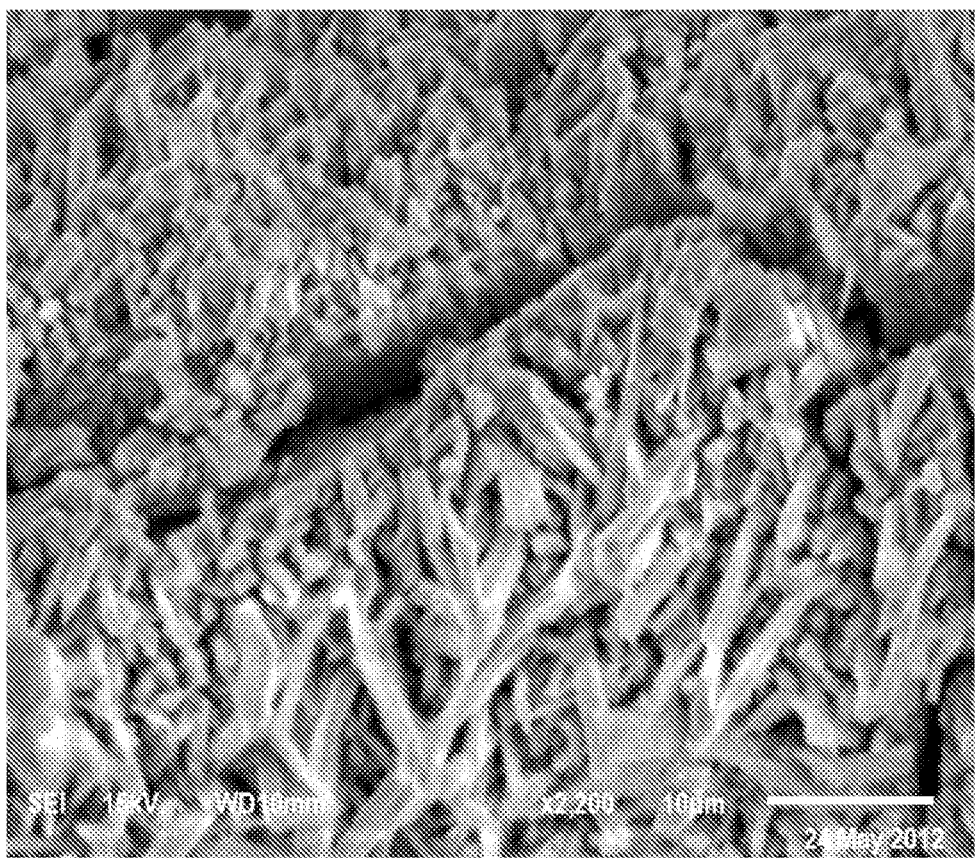

The oxidative furnacing produces a substantially uniform aluminum oxide outer layer on the steel fibers by oxidizing the residual aluminum left on the surface of the plurality of steel fibers after diffusion furnacing. The resulting aluminum oxide outer layer interfaces with (and is strongly adhered to) the aluminide layer. The interaction between the aluminum oxide outer layer and aluminide layer provides high temperature stability to the fibrous material. FIGS. 4B and 4C show SEM images of one of the thin steel fibers of the instant disclosure after the aluminum oxide outer layer has been formed.

In addition, the aluminum oxide outer layer is thick enough to act as a catalyst support with or without a washcoat layer. The thickness of this aluminum oxide outer layer can be controlled, by some degree, by adjusting the thickness of the initial aluminum coating, by the diffusion furnacing conditions, and by the degree of oxidation of the aluminum. Furthermore, the resulting surface area of the aluminum oxide outer layer can be controlled by adjusting the final calcination temperature or by adding stabilizing components (e.g., cerium oxide) in a small quantity, either to the coating slurry or introduced by impregnation as aqueous cerium salt solutions after the aluminum oxide coating is formed, followed by calcination.

The catalytic soot trap embodiment of the present invention is further illustrated in the non-limiting examples described below.

EXAMPLE 9

A ¼ inch thick×2 inch wide coarse, medium, or fine grade 430 or 434 coiled stainless steel mat is fed into a continuous falling film coater (no Mayer rods) and the mat is coated with an aluminicious slurry comprising 62% solids (aluminum powder; about 10 micron average particle size) and 10% methylacrylate-type binder in acetone, wherein the slurry has been previously ball milled with steel shot overnight. Cerium oxide is optionally added at a dosage of about 2% of the anticipated aluminum oxide. The slurry is continuously stirred during the coating process.

The coated steel fiber mat rises vertically at about six feet per minute to generate a substantially uniform coating by the falling film method. The web speed and vertical distance over which the falling film drops (i.e., the length of the zone before the dryer) can be optimized to adjust the thickness of the aluminicious slurry coating. After coating, the coated steel fiber mat moves vertically through a drying section to set the binder and then moves continuously through rubber pinch rollers to a retort under flowing hydrogen. The retort is housed in a clam-shell furnace that comprises a four-foot heated zone held at 730° Celsius. The steel fiber mat emerges into air and is cooled before traveling to an oxidative furnace operating under flowing air. Alternatively, the furnaced steel fiber mat can be fabricated into a soot trap form factor at this stage followed by oxidative furnacing of the fabricated part. The oxidative furnace is heated to about 800° Celsius to about 950° Celsius for continuous processing of a fiber mat. The steel fiber mat is exposed to the oxidative furnace for about 5 to about 15 minutes. A static furnace is used to oxidize pre-formed parts.

The product (i.e., mat of fibers) that emerges from the oxidative furnace can be coiled and cut to a desired length for fabrication into a soot trap. Once oxidized and fabricated, the formed soot trap component can be impregnated with catalytic agents and calcined using methods known in the art. For example, a simple catalytic soot trap (suitable as a test prototype) can be produced by taking the fibrous material after it emerges from the oxidative furnace, coiling it, cutting the coiled material, folding the coiled and cut material upon itself, rolling the folded material into a cylindrical shape and then sliding that cylindrical body into a 0.86 inch ID stainless steel tube cut to a 3-inch length. An aqueous solution of a platinum group metal(s) may then be impregnated into the formed soot trap and the form calcined.

In one aspect of the invention, the mat of thin steel fibers that emerges from the oxidative furnace is impregnated with a solution or suspension comprising a platinum group metal catalyst and then dried and, optionally, further heat treated to form the final catalytic fibrous material.

As used herein, the term "platinum group metal catalyst" means any platinum group metal compound or complex, which, upon calcination or use of the catalyst decomposes or otherwise converts to a catalytically active form. Water soluble compounds or water dispersible complexes as well as organic soluble or dispersible compounds or complexes of one or more platinum group metals may be utilized as long as the liquid used to impregnate or deposit the catalytic metal compounds onto the plurality of thin coated steel fibers does not adversely react with the catalytic metal or its compound or complex or the other components of the catalytic material, and is capable of being removed from the catalyst by volatilization or decomposition upon heating. In some instances, the completion of the removal of the liquid may not take place until the catalyst is placed into use and subjected to the high temperatures encountered during operation.

Typically, aqueous solutions of soluble compounds or complexes of the platinum group metals are preferred. For example, some of the compounds that may be used in the fibrous material of the instant disclosure include: gold (III) acetate, hydrogen tetrachloroaurate (III), ammonium hexachloroiridate (IV), iridium (III) chloride hydrate, ammonium tetrachloropalladate (II), palladium (II) nitrate, ammonium tetrachloroplatinate (II), dihydrogen hexachloroplatinate (IV) (chloroplatinic acid), tetraamineplatinum (II) nitrate, rhodium (III) chloride hydrate, potassium pentachlororhodate (III), rhodium nitrate, ruthenium (III) chloride, and pentaaminepyridineruthenium (II) tetrafluoborate. Additional compounds may be added as cocatalytic agents, promoters, or as modifiers along with the platinum group metal compounds. Separate impregnation steps may be necessary for certain added compounds that might react to form precipitates with the platinum group metal compounds. Examples of non-platinum group metal promoter/cocatalytic agent compounds include ammonium hexanitrocerrate (IV) and manganese (II) nitrate.

Once impregnation of the product (i.e., mat of steel fibers) that emerges from the oxidative furnace with the solution or suspension comprising a platinum group metal catalyst is complete, the product is calcined to convert the platinum group metal of the platinum group metal catalyst to a well dispersed form, which is either catalytically active or transforms to an active form in use.

After impregnation is complete, a filter may be formed from the fibrous material that is suitable for partial capture of soot particles from diesel engine exhaust. Some filter designs are known in the art for this purpose. These typically feature aspects such as partial bypass channels that enable approximately even distribution of captured particles throughout the depth of the filter element and serve to reduce pressure drop across the filter. After final treatment, fiber mats typically are compressed into relatively dense beds (of predefined densities) around the bypass structures, which can be corrugated metal spacers, tubular pipes, grooves in the housing, or similar features. The assembly then is fitted into a shroud of appropriate dimensions for attachment to engine exhaust manifolds. When in use, periodic or continuous catalytically initiated oxidation of embedded soot particles, under appropriate lean burn conditions, allows the filter element to destroy embedded soot and to reduce pressure drop caused by particulate buildup within the filter over time.

In another aspect of the disclosure, a filter is formed from the product that emerges from the oxidative furnace in a similar fashion to that described above. The filter (as an individual part) is then impregnated with a solution or suspension comprising a platinum group metal catalyst and, optionally, a promoter or co-catalytic agent, then heat treated as is appropriate to convert the catalyst precursors to active forms.

EXAMPLE 10

Laboratory Preparation and Characterization of Catalyst Support Fibers

Stainless steel grade 430 fibers of elliptical shape in the diameter range of approximately 125 to 220 micron were supplied by Ribbon Technology Corporation in the form of a loosely pressed mat. The mat was cut into eight inch strips approximately 3 inches wide, washed with acetone, and air dried. Each of several mat strips then were mounted into a laboratory-scale falling film dip coating machine and coated with a slurry composition consisting of 57.8% by weight aluminum metal powder (about 3 micron average particle size), 4.2% by weight methyl acrylate-based binder, and the balance acetone solvent. The coating slurry, prepared in a 900 mL batch, had been ball-milled overnight prior to coating using approximately 150 mL of ¼ inch diameter stainless steel balls as grinding/mixing media. After coating, each mat was hung vertically in a hot air stream to dry, then stapled or spot welded to a 2 mil thick low carbon steel foil leader. The composite assembly of leader and fiber mat was passed through a 4 foot furnace, which had been fitted with a steel retort, held at 710° C. under flowing hydrogen at a feed rate of 6 feet per minute. The furnaced mat was cooled in air and cut into various aliquots used for further work. In some cases, the furnaced, aluminized fibers first were formed into compressed cylinders suitable for filtration prior to further processing, and in other cases, the loosely pressed mats were oxidized directly, as described below, then formed.

In a first oxidation stage, the furnaced material was heated in air in a static oven ramped at 10° C. per minute between room temperature and 620° C., then held at 620° C. for 1.5 hours. In a second stage, the oven temperature was increased from 620° C. to 850° C. at a ramp rate of 8° C./minute then soaked at 850° C. for 20 minutes. The sample was then cooled to room temperature in air slowly, and held within the oven as it cooled. Oxidized fibers increased in weight by about 1% during this treatment. Oxidized fibers were characterized by SEM, EDS, and TGA techniques and some aliquots tested as catalyst supports in the form of fiber mats. FIG. 4 shows Scanning Electron Microscope images of the aluminum coated and oxidized fibers of this example compared to untreated fibers, as received. FIG. 4A shows the untreated control fibers as received. FIG. 4B shows a low magnification image of treated fibers after the oxidation step. FIG. 4C shows a high magnification image of treated fibers after the oxidation step. Surface analysis by the EDS technique corresponding to one of the images of the treated and oxidized fibers shows an oxygen to aluminum atomic ratio of 1.5, consistent with a surface composition rich in aluminum oxide.

The fiber mat catalyst supports produced above can be infiltrated with solutions or suspensions of catalyst materials (e.g., platinum group metal or "PGM" catalyst materials) and then dried to form catalytically active bodies. Alternatively, we contemplate that other methods known in the art may be suitable to load active catalytic species onto the support surfaces (e.g., chemical vapor deposition methods or supercritical precipitation methods).

Still other objects and advantages of the present disclosure will become readily apparent to those skilled in the art from the preceding detailed description, wherein it is shown and described in preferred embodiments, simply by way of illustration of the best mode contemplated. As will be realized the disclosure is capable of other and different embodiments, and its several details are capable of modifications in various obvious respects, without departing from the spirit or scope of the invention as set forth in the claims. Accordingly, the description is to be regarded as illustrative in nature and not as restrictive.

The term "comprising" (and its grammatical variations) as used herein is used in the inclusive sense of "having" or "including" and not in the exclusive sense of "consisting only of." The term "consisting essentially of" as used herein is intended to refer to that which is explicitly recited along with what does not materially affect the basic and novel characteristics of that recited or specified. The terms "a" and "the" as used herein are understood to encompass the plural as well as the singular.

We claim:

1. A method of producing a structured catalyst comprising:
   (a) preparing a slurry comprising one or more metal powders, including aluminum;
   (b) coating a metal substrate, or a mat of metal fiber or a woven metal fiber assembly, with said slurry;
   (c) subjecting the coated metal substrate, coated metal fiber mat or coated woven metal fiber assembly to heat under an inert or reducing atmosphere wherein at least one of the one or more metal powders melts and interdiffuses into the surface of the metal substrate, or metal fiber mat or woven metal fiber assembly;
   (d) leaching the coated metal substrate or coated metal fiber mat or coated woven metal fiber assembly obtained in step (c) in a caustic solution;
   (e) bathing the coated metal substrate, coated metal fiber mat or coated woven metal fiber assembly obtained in step (d) in a chelating acid solution;
   (f) passivating the coated metal substrate, coated metal fiber mat or coated woven metal fiber assembly obtained in step (e); and
   (g) optionally abrading the surface of the coated metal substrate obtained in step (f).

2. The method of claim 1, further comprising the following additional step to form a catalyst support:
   (h) subjecting the coated metal substrate, coated metal fiber mat or coated woven metal fiber assembly obtained after step (f) or step (g) to heat in an oxygen containing atmosphere for an additional period of time.

3. The method of claim 2, wherein the coated metal substrate, coated metal fiber mat or coated woven metal fiber assembly, after step (h), comprises an aluminum oxide coating as an outer layer and said method comprises the following additional step: impregnating at least a portion of the aluminum oxide outer layer with one or more catalytic substances.

4. The method of claim 1, further comprising forming the coated metal substrate, coated metal fiber mat or coated woven metal fiber assembly into a catalyst structure before leaching.

5. The method of claim 1, further comprising forming the coated metal substrate, coated metal fiber mat or coated woven metal fiber assembly into a catalyst structure after passivating or after abrading, if abrasion is performed.

6. The method of claim 1, wherein in step (c), the coated metal substrate, coated metal fiber mat or coated woven metal fiber assembly is subjected to heat in a reducing atmosphere.

7. The method of claim 1, wherein the metal of the metal substrate, mat of metal fiber or woven metal fiber assembly is either: (a) primarily nickel; or (b) a grade 430 stainless steel.

8. The method of claim 1, wherein, in addition to said aluminum, the one or more metal powders are selected from the group consisting of Zr, V, Cr, Co, Ti, W, Nb, Mo, and Ta.

9. The method of claim 1, wherein, in step (c), the coated metal substrate, coated metal fiber mat or coated woven metal fiber assembly is subjected to a temperature of about 650° C. to 950° C.

10. The method of claim 1, wherein the acid is mineral acid or a carboxylic acid.

11. The method of claim 1, wherein the coated metal substrate is passivated using a solution comprising $H_2O_2$.

12. The method of claim 1, wherein the one or more metal powders include powders made from alloys of two or more metals.

13. The method of claim 12, wherein said alloys include alloys made from Ni and Zr and alloys made from Ni and Cr.

14. A method of producing a structured catalyst support comprising:
   (a) preparing a slurry comprising one or more metal powders, including aluminum;
   (b) coating a metal substrate, or a metal fiber mat or a woven metal fiber assembly, with said slurry;
   (c) subjecting the coated metal substrate, coated metal fiber mat or coated woven metal fiber assembly to heat under an inert or reducing atmosphere wherein at least one of the one or more metal powders melts and interdiffuses into the surface of the metal substrate, or metal fiber mat or woven metal fiber assembly; and
   (d) subjecting the coated and heat treated metal substrate, metal fiber mat or woven metal fiber assembly to heat in an oxygen containing atmosphere for an additional period of time.

15. The method of claim 14, further comprising forming the coated metal substrate, coated metal fiber mat or coated woven metal fiber assembly into a catalyst structure after step (c).

16. The method of claim 14, further comprising forming the coated metal substrate, coated metal fiber mat or coated woven metal fiber assembly into a catalyst structure after step (d).

17. The method of claim 14, wherein the coated and heat treated metal substrate, metal fiber mat or woven metal fiber assembly obtained from step (d), comprises an aluminum oxide coating as an outer layer and said method comprises the following additional step: impregnating at least a portion of the aluminum oxide outer layer with one or more catalytic substances.

* * * * *